United States Patent
Kanu

(10) Patent No.: US 10,836,992 B2
(45) Date of Patent: Nov. 17, 2020

(54) ANAEROBIC DIGESTER

(71) Applicant: Ifeyinwa Rita Kanu, Edinburgh (GB)

(72) Inventor: Ifeyinwa Rita Kanu, Edinburgh (GB)

( * ) Notice: Subject to any disclaimer, the term of this patent is extended or adjusted under 35 U.S.C. 154(b) by 0 days.

(21) Appl. No.: 16/603,966

(22) PCT Filed: Apr. 10, 2018

(86) PCT No.: PCT/GB2018/050951
§ 371 (c)(1),
(2) Date: Oct. 9, 2019

(87) PCT Pub. No.: WO2018/189525
PCT Pub. Date: Oct. 18, 2018

(65) Prior Publication Data
US 2020/0115670 A1 Apr. 16, 2020

(30) Foreign Application Priority Data
Apr. 10, 2017 (GB) .................................. 1705768.8

(51) Int. Cl.
*C02F 3/28* (2006.01)
*C12M 1/00* (2006.01)
(Continued)

(52) U.S. Cl.
CPC ............... *C12M 45/20* (2013.01); *C02F 3/28* (2013.01); *C12M 21/04* (2013.01); *C12M 41/12* (2013.01);
(Continued)

(58) Field of Classification Search
CPC ...... C12M 45/20; C12M 21/04; C12M 47/18; C12M 41/12; C12M 45/02; C12M 45/06; C02F 3/28
(Continued)

(56) References Cited

U.S. PATENT DOCUMENTS

| | | | | |
|---|---|---|---|---|
| 4,632,758 A | * | 12/1986 | Whittle | C02F 1/20 210/151 |
| 8,835,155 B2 | * | 9/2014 | Dvorak | C12M 21/04 435/268 |
| 2003/0219467 A1 | * | 11/2003 | Miner | A61K 31/131 424/442 |

FOREIGN PATENT DOCUMENTS

| | | |
|---|---|---|
| WO | 2011/128781 | 10/2011 |
| WO | 2012/005833 | 1/2012 |
| WO | 2012/018908 | 2/2012 |

OTHER PUBLICATIONS

International Search Report for PCT/GB2018/050951 dated Aug. 29, 2018, 6 pages.
(Continued)

*Primary Examiner* — Fred Prince
(74) *Attorney, Agent, or Firm* — Joshua B. Brady; Nixon & Vanderhye, P.C.

(57) ABSTRACT

Anaerobic digestion apparatus comprises a first chamber for retaining organic matter before and/or during anaerobic digestion and a second chamber for retaining organic matter during anaerobic digestion. The anaerobic digestion apparatus is configured to refrigerate or heat the first chamber to suppress methanogenesis in the first chamber. The anaerobic digestion apparatus comprises a controller programmed to regulate the anaerobic digestion process and to thereby reduce system perturbations. The flow of organic matter to the second chamber where methanogenesis is regulated. There is disclosed an inoculum for anaerobic digestion comprising *Acetobacterium woodii* and *Methanosaeta concilii*.

19 Claims, 6 Drawing Sheets

(51) Int. Cl.
*C12M 1/107* (2006.01)
*C12M 1/34* (2006.01)
*C12M 1/33* (2006.01)

(52) U.S. Cl.
CPC ............ *C12M 45/02* (2013.01); *C12M 45/06* (2013.01); *C12M 47/18* (2013.01)

(58) Field of Classification Search
USPC .......................... 210/603, 612, 614, 175, 252
See application file for complete search history.

(56) References Cited

OTHER PUBLICATIONS

Written Opinion of the ISA for PCT/GB2018/050951 dated Aug. 29, 2018, 10 pages.

* cited by examiner

ANAEROBIC DIGESTER

This application is the U.S. national phase of International Application No. PCT/GB2018/050951 filed Apr. 10, 2018 which designated the U.S. and claims priority to GB Patent Application No. 1705768.8 filed Apr. 10, 2017, the entire contents of each of which are hereby incorporated by reference.

FIELD OF THE INVENTION

The invention relates to anaerobic digestion apparatus, methods of using anaerobic digestion apparatus in the anaerobic digestion of organic matter, apparatus and methods for generating methane from organic matter, apparatus and methods for producing renewable power from organic matter, apparatus and methods for generating electricity from organic matter, methods of hydrolysing organic matter, and microbiological cultures for use in the anaerobic digestion of organic matter.

BACKGROUND TO THE INVENTION

Anaerobic digestion refers to a collection of processes by which organic matter is broken down by microorganisms in the absence of oxygen. Anaerobic digestion involves the biochemical hydrolysis of organic polymers (such as carbohydrates and proteins) into small organic molecules, and the conversion of such small molecules into methane, carbon dioxide, nitrogen and hydrogen, as well as other by-products. Anaerobic digestion is used as part of a treatment process in the recycling of biodegradable waste matter such as food waste matter and sewage sludge. This process typically results in the production of biogas (comprising around 50% to 80% methane), as well as liquid and solid digestates. Since biogas can be used as a fuel, anaerobic digestion is considered a source of renewable energy. Biogas can be further refined to produce biomethane, which has a similar methane content to natural gas. Digestate can be useful as a nutrient-rich fertiliser, as well as a source of higher-value chemical products.

Controlled anaerobic digestion, as used in the production of biogas and biomethane, is typically carried out on an industrial scale using a combination of food waste collected from domestic and commercial properties, farm waste, specialised energy crops, manure and sewage sludge. Commercial anaerobic digesters typically make use of microorganisms which are pathogenic to humans and which are therefore unsuitable for use in domestic settings. Pathogenic hydrolytic microorganisms in particular are commonly used in commercial anaerobic digesters. Commercial anaerobic digesters are typically large and complex, and generally release unpleasant smells into the surrounding environment.

Accordingly, it would be beneficial to provide both anaerobic digesters and microbiological cultures which are safe and practical for use in domestic settings. It would also be beneficial to provide anaerobic digesters and microbiological cultures capable of more complete conversion of digester input materials to methane.

SUMMARY OF THE INVENTION

A first aspect of the invention provides anaerobic digestion apparatus (e.g. an anaerobic digester). The apparatus comprises a first chamber for retaining organic matter before and/or during anaerobic digestion and a second chamber for retaining organic matter during anaerobic digestion. The apparatus is typically configured to (i.e. in use) refrigerated or heat the (i.e. contents of) the first chamber, that is to say the first chamber is typically refrigerated or heated.

The temperature of the first chamber is refrigerated or heated (typically regulated) to a temperature which suppresses methanogenesis in the first chamber (e.g. reduced the rate of methane generation to below 10%, below 5% or preferably below 1% of the rate of methane generation in the second chamber). Thus, methanogensis takes place predominantly in the second chamber.

Methanogenesis may be suppressed by reducing the temperature in the first chamber to a temperature which suppresses methanogenesis by live methanogenic microorganisms which are present, or by the raising the temperature in the first chamber to a temperature which suppresses methanogenesis by live methanogenic microorganisms which are present or which kills methanogens.

The apparatus is typically configured to move organic matter from the first chamber to the second chamber and from the second chamber to the first chamber. Thus, methanogenic microorganisms from the second chamber are moved to the first chamber and, without the refrigeration or heating of the first chamber, there would be significant methanogenesis in the first chamber.

It will be understood that by anaerobic digestion we mean the process by which organic matter is broken down by microorganisms in the absence of oxygen. Microorganisms responsible for anaerobic digestion typically include anaerobic bacteria and/or anaerobic archaea. Anaerobic digestion typically includes one or more of the following processes: hydrolysis of large molecules (e.g. polymers such as carbohydrates (polysaccharides) and/or proteins (polypeptides) and/or lipids (such as triglycerides)) to form smaller molecules (e.g. simple sugars, amino acids and/or fatty acids); acidogenesis of the products of hydrolysis to form, for example, volatile fatty acids (VFAs); acetogenesis of the products of hydrolysis and/or acidogenesis to form acetic acid; and methanogenesis of the products of hydrolysis, acidogenesis and/or acetogenesis to form methane ($CH_4$). Controlled anaerobic digestion of organic matter is used in the production of biogas. Biogas is a mixture of a number of different gases but typically comprises at least 50% methane. Biogas may also comprise carbon dioxide ($CO_2$), nitrogen ($N_2$), hydrogen ($H_2$), hydrogen sulphide ($H_2S$) and/or oxygen ($O_2$).

The apparatus may be configured to refrigerate the first chamber to a temperature equal to or below 10° C., or equal to or below 8° C., or equal to or below 6° C., or equal to or below 4° C.

The apparatus may be configured to heat the first chamber to a temperature equal to or greater than 40° C., or equal to or greater than 50° C., or equal to or greater than 60° C.

The apparatus is typically configured for use in a two-stage anaerobic digestion process, that is to say where the initial phases of anaerobic digestion (including, for example, hydrolysis, acidogenesis and/or acetogenesis) take place in a first location (e.g. and substantially at the same time) and where methanogenesis subsequently takes place in a second location (i.e. at least partially) separated from the first location.

In the two-stage anaerobic digestion process, hydrolysis, acidogenesis and/or acetogenesis typically take place in the (refrigerated or heated) first chamber, and methanogenesis typically takes place in the second chamber. Hydrolytic, acidogenic and/or acetogenic microorganisms and/or enzymes (which together are typically responsible for hydrolysis, acidogenesis and/or acetogenesis of organic matter) are typically capable of withstanding, and indeed are able to proliferate at, lower temperatures than methanogenic microorganisms. Methanogenic microorganisms are typically inhibited at lower temperatures (e.g. below 10° C.) and tend to proliferate at higher temperatures (e.g. above 10° C.). Refrigeration of the first chamber typically means that organic matter can be moved between the first and second chambers (and vice versa) during anaerobic digestion while ensuring that methanogenesis takes place predominantly in the second chamber and not in the first chamber. In the alternative, heating of the second chamber to a sufficient temperature to inhibit or kill the methanogenic microorganisms, but where hydrolytic, acidogenic and/or acetogenic microorganisms and/or enzymes are functional, also enables methanogenesis to take place predominantly in the second chamber while allowing organic matter to be moved between the first and second chambers (and vice versa).

The inventor has found that by separating (i.e. spatially) the process of methanogenesis from that of hydrolysis, acidogenesis and/or acetogenesis, more complete methanogenesis of the organic matter is possible. This is because key process parameters, such as volatile fatty acid (VFA) concentration (VFAs (and principally acetic acid) being produced during hydrolysis, acidogenesis and/or acetogenesis), nitrogen concentration and pH, to which methanogenic microorganisms are particularly sensitive, can be more accurately controlled in the region in which methanogenesis occurs by regulating the flow of digestate between the first and second chambers. The process parameters can be optimised to maximise methane output and control system perturbations.

Accordingly, both the first chamber and the second chamber are typically digestion chambers, i.e. chambers in which one or more stages of anaerobic digestion take place in use.

In addition, the first chamber may in practice function as a storage chamber for organic matter prior to anaerobic digestion. Where the first chamber functions as a storage chamber, refrigeration of said first chamber slows down decomposition of organic matter retained therein and therefore reduces the release of unpleasant smells from the apparatus into the surrounding environment. This is important where the apparatus is used in a domestic setting, for example. It may be necessary to store organic matter in the first chamber for many hours prior to anaerobic digestion, for example in order to take advantage of cheaper off-peak periods for electricity supply.

It will therefore be understood that the first chamber retaining organic matter "before and/or during" anaerobic digestion refers to the first chamber retaining organic matter either before anaerobic digestion or during anaerobic digestion, or both before and during anaerobic digestion.

However, the apparatus may comprise a storage chamber, into which (typically macerated) waste is received before it is transferred into the first chamber (in some embodiments via a said pasteurisation chamber). The apparatus may comprise a controllable pump configured to transfer organic matter into the first chamber for anaerobic digestion. The storage chamber may be refrigerated. The apparatus may comprise means for refrigerating the storage chamber.

The apparatus may comprise means for refrigerating the first chamber. The apparatus may comprise a heat pump configured to refrigerate the first digestion chamber. The means for refrigerating the first chamber may comprise one or more of the following: vapour-compression apparatus (as is commonly used in domestic refrigerators), vapour-absorption apparatus, thermoelectric cooling apparatus (as used in Peltier refrigerators).

The apparatus may comprise means for heating the first chamber. Hydrolysis and acidogenesis may therefore be carried out at a raised temperature. The apparatus may be adapted to pasteurise matter in the first chamber, for example to heat it to above a threshold temperature (typically greater than or equal to 40° C., greater than or equal to 50° C. or greater than or equal to 60° C.) for at least a predetermined period of time (e.g. an hour or more). This may be carried out at the same time as hydrolysis and acidogenesis, or subsequently.

The apparatus may comprise a buffer chamber connected to the first and second chambers, through which organic matter is moved from the first chamber to the second chamber. It may be that the apparatus is configured to pasteurise organic matter in the buffer chamber (for example to heat it to a predetermined temperature, which is typically at least 60° C., for a predetermine time, for example at least an hour).

The apparatus may comprise a pasteurisation chamber into which (e.g. macerated) organic waste is received prior to transfer to the first chamber for digestion. Said pasteurisation chamber may be heated to above a threshold temperature (e.g. 60° C. or higher) for at least a predetermined period of time (e.g. an hour or more). The resulting pasteurised matter may then be transferred to the first chamber for hydrolysis and acidogenesis.

The first chamber may be thermally insulated. The first chamber may be formed from thermally insulating material. The first chamber may be (i.e. at least partially) surrounded by thermally insulating material.

The second chamber may be thermally insulated. The second chamber may be formed from thermally insulating material. The second chamber may be (i.e. at least partially) surrounded by thermally insulating material.

The first and second chambers may be thermally insulated from one another. Thermally insulating material may be provided between the first and second chambers.

The apparatus typically comprises an inlet through which organic matter may be introduced. The inlet may extend (i.e. directly) into the first chamber. The inlet may be (i.e. at least partially) sealable. The inlet may comprise an airtight seal. Sealing the inlet typically inhibits unpleasant smells from escaping from the apparatus to the surrounding environment.

The apparatus typically comprises a macerator for macerating organic matter prior to anaerobic digestion. The skilled person will understand that by maceration we refer to cutting up or chopping organic matter solids to reduce solid particle size. The macerator may comprise one or more blades. The one or more blades may be rotatable. The macerator may comprise a chopper pump. The apparatus may comprise a maceration chamber in which the macerator is provided. The inlet may extend (i.e. directly) into the maceration chamber such that that organic matter may be introduced into the maceration chamber. A conduit may be provided between the maceration chamber and the first chamber (or the storage chamber where present) such that (i.e. macerated) organic matter may be moved from the maceration chamber into the first chamber. The maceration chamber may be provided (i.e. vertically) above the first chamber (or storage chamber where present) such that (i.e. macerated) organic matter falls and/or flows into the first chamber (or storage chamber where present) from the maceration chamber under gravity.

The apparatus may comprise a source of water, such as one or more water sprays. The source of water (e.g. the one or more water sprays) may be configured to (i.e. in use)

direct (e.g. spray) water onto at least a portion of the macerator (e.g. the one or more blades). Directing water onto at least a portion of the macerator typically facilitates passage of organic matter through the macerator and reduces clogging. Addition of water to the (i.e. macerated) organic matter typically assists in the formation of an organic matter slurry for easier anaerobic digestion of the organic matter present. Addition of water may also be used to adjust the nitrogen concentration of the organic matter slurry.

The source of water (e.g. the one or more water sprays) may be configured to (i.e. in use) direct (e.g. spray) water into the first chamber.

A conduit may extend between the first and second chambers (i.e. from the first chamber to the second chamber, whether directly or through at least one further (e.g. buffer) chamber) such that organic matter may be moved between the said first and second chambers through the said conduit. The apparatus may comprise organic matter flow regulation means (e.g. an organic matter flow regulator) for regulating the movement of organic matter between the first and second chambers through the conduit. The organic matter flow regulation means may comprise (e.g. consist of) a pump. The pump may be a two-way pump, i.e. such that organic matter may be pumped from the first chamber into the second chamber and from the second chamber into the first chamber.

The first and second chambers may be located (i.e. horizontally) adjacent to one another. The conduit between the first and second chambers may extend substantially horizontally between the said first and second chambers.

The second chamber is typically not refrigerated.

The apparatus may be configured to regulate the temperature of the (e.g. contents of the) second chamber to be higher than the ambient temperature (i.e. the temperature of the surrounding environment). The apparatus may be configured to regulate the temperature of the (e.g. contents of the) second chamber to be higher than the temperature of (e.g. the contents of) the first chamber. The apparatus may be configured to regulate the temperature of the (e.g. contents of the) second chamber to be higher than the temperature of the (e.g. contents of the) first chamber by at least 10° C. However, where the first chamber is heated to suppress methanogenesis it may be that the apparatus is configured to regulate the temperature of the (e.g. contents of the) first chamber to be higher than the temperature of the (e.g. contents of the) second chamber, by at least 10° C.

The apparatus may be configured to heat the (e.g. contents of the) second chamber, that is to say the second chamber may be heated. The apparatus may be configured to heat the (e.g. contents of the) second chamber to a temperature greater than 10° C., or greater than 15° C., or greater than 20° C., or greater than 25° C., or greater than 30° C. However, the temperature to which the (e.g. the contents of the) second chamber is heated may for example be below 50° C. or typically below 40° C. Since methanogenic microorganisms typically proliferate at higher temperatures (e.g. above 10° C.), heating the second chamber relative to the first chamber typically encourages methanogenic microorganisms to proliferate to a significantly greater extent within the second chamber compared to the refrigerated first chamber.

The apparatus may be configured to transfer (e.g. feed) organic matter (e.g. with acetogenic and methanogenic microorganisms) from the first chamber into the second chamber whether directly or through one or more further chambers (e.g. a buffer chamber). The apparatus may be configured to transfer organic matter (e.g. with acetogenic and methanogenic microorganisms) from the second chamber into the first chamber whether directly or through one or more further chambers (e.g. a buffer chamber). The apparatus may be configured to transfer (e.g. circulate) organic matter (e.g. with acetogenic and methanogenic microorganisms) back and forth between the first and second chambers whether directly or through one or more further chambers (e.g. a buffer chamber). When organic matter is moved (e.g. circulated) between the first and second chambers, acidogenesis and acetogenesis typically take place (i.e. predominantly) in the first chamber and methanogenesis typically takes places (i.e. predominantly) in the second chamber (since the methanogenic microorganisms are typically less active in the first chamber due to the lower temperature, where the first chamber is refrigerated, or less active or killed in the second chamber by the higher temperature, where the first chamber is heated).

The apparatus may comprise means for heating the second chamber. The apparatus may comprise means for heating the contents of the second chamber. The apparatus may comprise a heater configured to (i.e. in use) heat the (e.g. contents of the) second chamber. The apparatus may comprise one or more heating elements configured to (i.e. in use) heat the (e.g. contents of the) second chamber.

The apparatus may comprise means for agitating the organic matter within the first chamber. For example, the apparatus may comprise one or more paddles provided within the first chamber. The one or more paddles may be movable (e.g. rotatable) such that movement (e.g. rotation) of the one or more paddles causes agitation (e.g. mixing) of the contents of the first chamber.

The apparatus may comprise means for agitating the organic matter within the second chamber. For example, the apparatus may comprise one or more paddles provided within the second chamber. The one or more paddles may be movable (e.g. rotatable) such that movement (e.g. rotation) of the one or more paddles causes agitation (e.g. mixing) of the contents of the second chamber.

The first chamber may be removable (e.g. replaceable). The second chamber may be removable (e.g. replaceable). The first and/or second chambers may be removable to permit cleaning or repair of the apparatus. Removal and/or replacement of the second chamber may also be necessary to remove excess solid and/or liquid digestate from the apparatus, or to introduce fresh microbiological inoculum into the apparatus.

The apparatus may comprise a gas purifier. The gas purifier may comprise one or more filters. The one or more filters may be configured to (e.g. selectively) remove one or more (i.e. gaseous) species from gases produced during anaerobic digestion of organic matter in the first and/or second chambers. The one or more filters may be configured to (e.g. selectively) remove one or more of the following species: carbon dioxide ($CO_2$), hydrogen sulphide ($H_2S$), ammonia ($NH_3$). The one of more filters may comprise carbon (e.g. activated carbon, charcoal). The one or more filters may comprise potassium permanganate.

The apparatus may comprise a gas purification chamber in which the gas purifier (i.e. the one or more filters) is located. The apparatus may comprise one or more conduits extending between the first chamber and the gas purification chamber (i.e. from the first chamber to the gas purification chamber) and/or between the second chamber and the gas purification chamber (i.e. from the second chamber to the gas purification chamber) such that gases may be transported between the said first chamber and the gas purification chamber and/or between the said second chamber and the gas purification chamber.

The apparatus may comprise a generator. The generator is typically configured to receive a flow of gas (e.g. biogas, that is to say at least predominantly methane gas) from the first chamber and/or from the second chamber and/or from the gas purifier (e.g. the gas purification chamber). The generator may be configured to combust the gas received. The generator may be configured to output electricity and/or heat generated by combustion of the gas. The generator may be a combined heat and power (CHP) generator. The generator may be a micro combined heat and power (micro-CHP) generator.

The apparatus may comprise a gas storage chamber (i.e. a gas accumulator). The gas storage chamber (i.e. the gas accumulator) is typically configured for storing gas before it is pumped into the generator. The gas storage chamber is typically configured (e.g. sized) to store less than 250 L, or more typically less than 200 L, or more typically less than 150 L, of gas. The gas storage chamber may be configured (e.g. sized) to store approximately 100 L of gas.

The generator may be configured to receive a flow of natural gas (e.g. from a mains gas supply). The generator may be configured to receive first and second gas flows, the first gas flow being a flow of gas (e.g. biogas) from the first chamber and/or from the second chamber and/or from the gas purifier (e.g. the gas purification chamber) and/or the gas storage chamber (e.g. the gas accumulator) and the second gas flow being a flow of natural gas (e.g. from the mains gas supply). The apparatus (e.g. the generator) may comprise a gas flow regulator (e.g. a valve, for example a solenoid valve) configured to regulate the first and/or second gas flows into the generator.

The generator is typically able to combust both natural gas and biogas produced by anaerobic digestion in the first and/or second chambers because the biogas has a high methane content with a calorific value (typically 30 MJ/$m^3$ to 34 MJ/$m^3$) similar to that of natural gas (typically 37.5 MJ/$m^3$).

The apparatus (e.g. the gas flow regulator) may be configured to permit flow of gas from the gas storage chamber (e.g. the gas accumulator) into the generator when the volume of gas stored in the gas storage chamber exceeds a threshold volume. The apparatus (e.g. the gas flow regulator) may be configured to restrict (e.g. prevent) flow of gas from the gas storage chamber (e.g. the gas accumulator) into the generator when the volume of gas stored in the gas storage chamber falls below a minimum volume. The apparatus (e.g. the gas flow regulator) may be configured to permit flow of natural gas (e.g. from the mains gas supply) into the generator when the flow of gas from the gas storage chamber into the generator is restricted (e.g. prevented), for example when the volume of gas stored in the gas storage chamber falls below the minimum volume. The apparatus (e.g. the gas flow regulator) may be configured to restrict (e.g. prevent) flow of natural gas (e.g. from the mains gas supply) into the generator when flow of gas from the gas storage chamber (e.g. the gas accumulator) is permitted, e.g. when the volume of gas stored in the gas storage chamber exceeds the threshold volume.

The generator may be connected to an electrical grid so that electricity generated by the generator can be fed into the grid, for example using a net meter.

The generator typically consumes approximately 600 L of gas (i.e. natural gas and/or biogas) per hour to produce 1 kWe of electricity and 5.5 kW of heat.

The apparatus typically generates 100 L of biogas per kg of organic matter processed.

The apparatus may comprise one or more sensors. The one or more sensors may be configured to measure one or more anaerobic digestion process parameters.

The one or more sensors may be configured to measure a parameter indicative of the volume of material (e.g. organic matter and/or organic matter slurry comprising organic matter and water) in the first chamber, and/or buffer chamber where present. The one or more sensors may be configured to measure a parameter indicative of the mass of material (e.g. organic matter and/or organic matter slurry comprising organic matter and water) in the first chamber, and/or buffer chamber where present.

The one or more sensors may be configured to measure one or more parameters indicative of the composition of material (e.g. organic matter and/or organic matter slurry comprising organic matter and water) retained within the first chamber and/or buffer chamber where present. The one or more sensors may be configured to measure one or more parameters indicative of the amount (e.g. concentration) of protein in material (e.g. organic matter and/or organic matter slurry comprising organic matter and water) retained within the first chamber and/or buffer chamber where present. The one or more sensors may be configured to measure one or more parameters indicative of the amount (e.g. concentration) of nitrogen-containing species (e.g. molecules, compounds, etc) in material (e.g. organic matter and/or organic matter slurry comprising organic matter and water) retained within the first chamber and/or buffer chamber where present. The one or more sensors may be configured to measure one or more parameters indicative of the amount (e.g. concentration) of nitrogen in material (e.g. organic matter and/or organic matter slurry comprising organic matter and water) retained within the first chamber and/or buffer chamber where present. The one or more sensors may comprise (e.g. consist of) one or more Kjeldahl probes. The one or more sensors may comprise (e.g. consist of) one or more ammonia-specific ion electrodes. The one or more sensors may be configured to measure one or more parameters indicative of the amount (e.g. concentration) of carbohydrate in material (e.g. organic matter and/or organic matter slurry comprising organic matter and water) retained within the first chamber and/or buffer chamber where present. The one or more sensors may be configured to measure one or more parameters indicative of the amount (e.g. concentration) of lipids (e.g. fats) in material (e.g. organic matter and/or organic matter slurry comprising organic matter and water) retained within the first chamber and/or buffer chamber where present.

The one or more sensors may be configured to measure a parameter indicative of the concentration of one or more fatty acids (i.e. volatile fatty acids) in material (e.g. organic matter and/or organic matter slurry comprising organic matter and water) in the first chamber and/or buffer chamber where present. For example, the one or more sensors may be configured to measure a parameter indicative of the concentration of formic acid ($CH_2O_2$), acetic acid ($C_2H_4O_2$), propionic acid ($C_3H_6O_2$), butyric acid ($C_4H_8O_2$) and/or valeric acid ($C_5H_{10}O_2$) in material (e.g. organic matter and/or organic matter slurry comprising organic matter and water) in the first chamber and/or buffer chamber where present. The one or more sensors may comprise (e.g. consist of) a volatile fatty acid (VFA) sensor which senses one or more (or any) volatile fatty acids, for example an optical VFA sensor (such as a VFA sensor comprising a Fabry-Perot spectrometer and/or an attenuated total reflectance (ATR)

probe). The VFA sensor may be an acetic acid sensor, for example an optical (typically infra-red) acetic acid sensor. As acetic acid is typically the predominant VFA, it can in some embodiments be sufficient to measure acetic acid.

The one or more sensors may be configured to measure a parameter indicative of the pH of material (e.g. organic matter and/or organic matter slurry comprising organic matter and water) in the first chamber and/or buffer chamber where present. The one or more sensors may be pH sensors, for example pH meters.

The one or more sensors may be configured to measure a parameter indicative of the temperature of the (e.g. contents of the) first chamber and/or buffer chamber where present (for example, a temperature of material (e.g. organic matter and/or organic matter slurry comprising organic matter and water) in the first chamber and/or buffer chamber where present). The one or more sensors may be temperature sensors. For example, the one or more sensors may comprise (e.g. consist of) one or more thermistors, thermocouples or resistance thermometers.

The one or more sensors may be configured to measure a parameter indicative of the volume of material (e.g. organic matter and/or organic matter slurry comprising organic matter and water) in the second chamber. The one or more sensors may be configured to measure a parameter indicative of the mass of material (e.g. organic matter and/or organic matter slurry comprising organic matter and water) in the second chamber.

The one or more sensors may be configured to measure one or more parameters indicative of the composition of material (e.g. organic matter and/or organic matter slurry comprising organic matter and water) retained within the second chamber. The one or more sensors may be configured to measure one or more parameters indicative of the amount (e.g. concentration) of protein in material (e.g. organic matter and/or organic matter slurry comprising organic matter and water) retained within the second chamber. The one or more sensors may be configured to measure one or more parameters indicative of the amount (e.g. concentration) of nitrogen-containing species (e.g. molecules, compounds, etc) in material (e.g. organic matter and/or organic matter slurry comprising organic matter and water) retained within the second chamber. The one or more sensors may be configured to measure one or more parameters indicative of the amount (e.g. concentration) of nitrogen in material (e.g. organic matter and/or organic matter slurry comprising organic matter and water) retained within the second chamber. The one or more sensors may comprise (e.g. consist of) one or more Kjeldahl probes. The one or more sensors may comprise (e.g. consist of) one or more ammonia-specific ion electrodes. The one or more sensors may be configured to measure one or more parameters indicative of the amount (e.g. concentration) of carbohydrate in material (e.g. organic matter and/or organic matter slurry comprising organic matter and water) retained within the second chamber. The one or more sensors may be configured to measure one or more parameters indicative of the amount (e.g. concentration) of lipids (e.g. fats) in material (e.g. organic matter and/or organic matter slurry comprising organic matter and water) retained within the second chamber.

The one or more sensors may be configured to measure a parameter indicative of the concentration of one or more fatty acids (i.e. volatile fatty acids) in material (e.g. organic matter and/or organic matter slurry comprising organic matter and water) in the second chamber. For example, the one or more sensors may be configured to measure a parameter indicative of the concentration of formic acid ($CH_2O_2$), acetic acid ($C_2H_4O_2$), propionic acid ($C_3H_6O_2$), butyric acid ($C_4H_8O_2$) and/or valeric acid ($C_6H_{10}O_2$) in material (e.g. organic matter and/or organic matter slurry comprising organic matter and water) in the second chamber. The one or more sensors may comprise (e.g. consist of) a volatile fatty acid (VFA) sensor, for example an optical VFA sensor (such as a VFA sensor comprising a Fabry-Perot spectrometer and/or an attenuated total reflectance (ATR) probe).

The one or more sensors may be configured to measure a parameter indicative of the pH of material (e.g. organic matter and/or organic matter slurry comprising organic matter and water) in the second chamber. The one or more sensors may be pH sensors, for example pH meters.

The one or more sensors may be configured to measure a parameter indicative of the temperature of the (e.g. contents of the) second chamber (for example, a temperature of material (e.g. organic matter and/or organic matter slurry comprising organic matter and water) in the second chamber). The one or more sensors may be temperature sensors. For example, the one or more sensors may comprise (e.g. consist of) one or more thermistors, thermocouples or resistance thermometers.

The apparatus may comprise a controller. The controller may be configured to receive measurements of one or more parameters from the one or more sensors. The controller may be configured to cause a change in the operation of the apparatus responsive to the received measurements. For example, the controller may be configured to receive measurements of the temperature of the first chamber and to regulate the operation of the means for refrigerating or heating (as appropriate) the first chamber responsive to the received temperature measurement. The controller may be configured to regulate (i.e. cause a change in) the movement of organic matter (e.g. organic matter slurry) between the first and second chambers (and/or between the buffer chamber and the second chamber where the buffer chamber is present) responsive to received measurements of one or more parameters (such as the volume, mass, composition, protein concentration, concentration of nitrogen-containing species, nitrogen concentration, carbohydrate concentration, lipid (e.g. fat) concentration, fatty acid (i.e. volatile fatty acid) concentration, and/or pH of material (e.g. organic matter and/or organic matter slurry comprising organic matter and water) in the first and/or second chamber and/or buffer chamber, where present).

Accordingly, the controller typically controls the rate of transfer of organic matter to the second chamber taking into account measurement made of one or more parameters of material which has been subject to hydrolysis and acidogenesis.

The controller may be a programmable logic controller (PLC). The controller may comprise a processor (e.g. a microprocessor).

The controller may be a proportional-integral-derivative (PID) controller. The skilled person will understand that a PID controller is a controller which makes use of a control loop feedback mechanism in which an error value is calculated as the difference between a desired system set point and a measured process variable and a system correction is applied based on proportional, integral and derivative terms. However, more typically the controller is an intelligent controller. The skilled person will understand that an intelligent controller is a controller which makes use of some form of artificial intelligence in order to regulate the system. Possible artificial intelligence methods used by the intelligent controller include neural networks, Bayesian probability, fuzzy logic, machine learning, evolutionary computation and genetic algorithms.

The apparatus may comprise a signal transmitter and/or a signal receiver. For example, the apparatus may comprise a wireless network transmitter and/or receiver, or a Bluetooth transmitter and/or receiver. The controller may be configured (e.g. programmed) to communicate with a remote device (such as a personal computer, tablet computer and/or mobile telephone) using the transmitter and/or receiver.

The controller may be programmed to send and receive signals to and from the remote device in response to one or more outputs from the one or more sensors. For example, the controller may be programmed to send an alert to the remote device if the nitrogen concentration and/or the VFA concentration in the first and/or second chambers exceeds a critical threshold value, and/or if the volume of material in the second digestion chamber exceeds a critical value, or if the one or more gas sensors detect methane outside the apparatus.

The apparatus may comprise one or more gas sensors (e.g. one or more methane sensors) configured to detect (e.g. measure the concentration of) one or more gases (e.g. methane) outside the first and/or second chambers (e.g. outside the apparatus). The controller is typically configured to receive one or more outputs from the one or more gas sensors. The controller may be configured to reduce the temperature of the first and/or second chambers if the one or more gas sensors detect methane outside the said first and/or second chambers (or outside the apparatus). The controller may be configured to reduce the temperature of the first and/or second chambers to below 10° C., or below 8° C., or below 6° C., or below 4° C., if the one or more gas sensors detect methane outside the first and/or second chambers (e.g. outside the apparatus). Additionally or alternatively, the controller may be configured to reduce the temperature of the first and/or second chambers if the nitrogen concentration and/or the VFA concentration (e.g. the acetate concentration) in the first and/or second chambers exceeds a critical threshold value and/or if the volume of material in the second digestion chamber exceeds a critical value.

The apparatus (e.g. the controller) may comprise a clock. The apparatus (e.g. the controller) may comprise a timer. The controller may be configured (e.g. programmed) to regulate the movement of organic matter between the first and second chambers based on an output from the clock or timer.

The apparatus may comprise an external housing. The external housing may be configured (e.g. shaped and dimensioned) to house (i.e. retain) the first and second chambers. The external housing may be further configured to retain, where present, the macerator (and, if present, the maceration chamber), the controller, the gas purifier (and, if present, the gas purification chamber), the gas storage chamber and/or the generator. The inlet may extend through an external wall of the external housing.

The external housing may be configured to retain, where present, the macerator (and, if present, the maceration chamber), the controller, the gas storage chamber and/or the gas purifier (and, if present, the gas purification chamber), but not the generator.

That is to say that it may be that the external housing retains most or all of other apparatus components except for the generator, i.e. the generator is provided separately from the other components.

The first chamber may be sealed (i.e. sealed from the surrounding environment). The second chamber may be sealed (i.e. sealed from the surrounding environment). Sealing the first and/or second chambers typically reduces escape of unpleasant smells and/or microorganisms into the surrounding environment. Alternatively, the first chamber may be unsealed (e.g. the inlet into the first chamber is not sealed) but, due to refrigeration of said first chamber, escape of unpleasant gases into the surrounding environment is still restricted.

The apparatus may be plumbed into the mains water supply. The apparatus may be electrically connected to the mains electricity supply.

The apparatus may comprise one or more anaerobic microorganisms.

The apparatus may comprise acetogenic microorganisms. The acetogenic microorganisms may comprise (e.g. consist of) acetogenic bacteria. The acetogenic microorganisms may comprise (e.g. consist of) acetogenic bacteria belonging to the genus *Acetobacterium*. The acetogenic microorganisms may comprise (e.g. consist of) acetogenic bacteria belonging to the species *Acetobacterium woodii*.

The acetogenic microorganisms may also be acidogenic microorganisms. The acetogenic bacteria are typically homoacetogenic. The acetogenic bacteria may also be acidogenic. The acetogenic bacteria belonging to the genus *Acetobacterium* may also be acidogenic. Acetogenic bacteria belonging to the species *Acetobacterium woodii* are also typically acidogenic.

The apparatus may comprise methanogenic microorganisms. The methanogenic microorganisms may comprise (e.g. consist of) methanogenic archaea. The methanogenic microorganisms may comprise (e.g. consist of) methanogenic archaea belonging to the genus *Methanosaeta*. The methanogenic microorganisms may comprise (e.g. consist of) methanogenic archaea belonging to the species *Methanosaeta concilii*.

The apparatus may comprise methanogenic microorganisms (e.g. methanogenic archaea) which are inhibited (e.g. which do not proliferate) at the temperature of the first chamber (i.e. the temperature to which the first chamber is refrigerated or heated).

The apparatus may comprise a microbiological culture comprising predominantly bacteria belonging to the genus *Acetobacterium* and archaea belonging to the genus *Methanosaeta*. The microbiological culture may comprise predominantly bacteria belonging to the species *Acetobacterium* and archaea belonging to the species *Methanosaeta concilii*.

The size of the apparatus may be defined with reference to three dimensions: the height of the apparatus (i.e. the maximum extension of the apparatus along a vertical direction when the apparatus is positioned in normal use), the breadth of the apparatus (i.e. the maximum extension of the apparatus along a first horizontal direction when the apparatus is positioned in normal use) and the depth of the apparatus (i.e. the maximum extension of the apparatus along a second horizontal direction, perpendicular to said first horizontal direction, when the apparatus is positioned in normal use). The apparatus is typically less than 3 metres, or less than 2 metres, or less than 1 metre, or less than 0.5 metres in (i.e. vertical) height. The apparatus typically has a breadth of less than 3 metres, or less than 2 metres, or less than 1 metre, or less than 0.5 metres. The apparatus typically has a depth of less than 3 metres, or less than 2 metres, or less than 1 metre, or less than 0.5 metres. The apparatus typically occupies of a volume of less than 15 cubic metres, or less than 10 cubic metres, or less than 5 cubic metres, or less than 3 cubic metres, or less than 1 cubic metre.

The apparatus may be domestic apparatus, that is to say apparatus configured for use in a domestic setting (e.g. a domestic residence). The apparatus may be kitchen apparatus, that is to say apparatus configured for use in a kitchen.

A second aspect of the invention provides a method of using the anaerobic digestion apparatus according to the first aspect of the invention in the anaerobic digestion of organic matter, the method comprising the steps of: exposing the organic matter to acetogenic microorganisms in the first chamber; transferring at least a portion of the organic matter from the first chamber into the second chamber; and exposing the said at least a portion of the organic matter to methanogenic microorganisms in the second chamber. Organic matter may be transferred from the first chamber directly into the second chamber or via one or more further chambers.

The method may comprise the step of macerating (e.g. chopping up) the organic matter. The step of macerating the organic matter typically occurs prior to exposing the organic matter to acetogenic microorganisms in the first chamber. The method may comprise the step of adding water to the organic matter (for example, mixing the organic matter with water). Water may be added to the organic matter during the maceration step and/or after maceration. Water may be added to the organic matter in the first chamber.

The method may comprise refrigerating the first chamber. The method may comprise refrigerating the first chamber to a temperature equal to or below 10° C., or equal to or below 8° C., or equal to or below 6° C., or equal to or below 4° C.

Alternatively, the method may comprise heating the first chamber to a temperature equal to or greater than 40° C., or equal to or greater than 50° C., or equal to or greater than 60° C.

The method typically also comprises transferring at least a portion of the organic matter from the second chamber (back) into the first chamber, such that methanogenic microorganisms are transferred into the first chamber from the second chamber, but wherein due to the regulation of the temperature (refrigeration or heating) of the first chamber, methanogenesis takes place predominantly in the second chamber. Thus, methanogenesis which would otherwise occur due to methanogenic microorganisms being transferred from the second chamber to the first chamber is suppressed in the first chamber by the refrigeration or heating of the first chamber.

This can enable movement of organic matter which is being digested back from the second chamber to the first chamber, e.g. to provide a supply of further microorganisms to the first chamber for further anaerobic digestion.

The method may comprise storing organic matter in the first chamber prior to exposure to acetogenic and/or methanogenic microorganisms. The method may comprise storing organic matter in the first chamber (or storage chamber where present) during the daytime (e.g. during daylight hours).

The method may comprise agitating (e.g. mixing) the organic matter (e.g. a slurry of organic matter and water) in the first chamber.

The method may comprise exposing the organic matter to one or more hydrolytic enzymes (i.e. hydrolases). The one or more hydrolytic enzymes may comprise one or more of the following: amylases, proteases, lipases, cellulases. The method may comprise exposing the organic matter to the one or more hydrolytic enzymes in the first chamber. The step of exposing the organic matter to one or more hydrolytic enzymes may take place before and/or during the step of exposing the organic matter to acetogenic microorganisms.

The method may comprise heating the second chamber. The method may comprise heating the second chamber to a temperature greater than 10° C., or greater than 15° C., or greater than 20° C., or greater than 25° C., or greater than 30° C.

The second chamber may be thermoregulated to within a temperature range selected to maximise methanogenesis in the second chamber.

The method may comprise agitating (e.g. mixing) the organic matter (e.g. a slurry of organic matter and water) in the second chamber.

The method may comprise transferring a portion of the organic matter in the first chamber from said first chamber into the second chamber. The method may comprise transferring a first portion of the organic matter in the first chamber from said first chamber into the second chamber and subsequently transferring a second portion of the remaining organic matter in the first chamber from said first chamber into the second chamber. The method may comprise sequentially transferring (i.e. feeding) three or more portions of the organic matter in the first chamber from said first chamber into the second chamber.

The method may comprise transferring a portion of the organic matter in the second chamber from said second chamber (e.g. back) into the first chamber. The method may comprise repeatedly (e.g. cyclically) transferring organic matter back and forth between the first and second chambers. The method may comprise transferring organic matter (e.g. back and forth) between the first and second chambers repeatedly (e.g. for example at least two times, but more typically three or more, four or more, or five or more times) within a 24 hour period. The method may comprise transferring organic matter (e.g. back and forth) between the first and second chambers repeatedly (e.g. for example at least two times, but more typically three or more, four or more, or five or more times) overnight. Organic matter may be transferred between the first and second chambers (e.g. periodically) (e.g. from the first chamber to the second chamber) based on an output from the clock or timer. Organic matter may be transferred between the first and second chambers approximately every hour, or every two hours, or every three hours, within the 24 hour period and/or overnight.

The method may comprise the one or more sensors measuring one or more parameters indicative of volume, mass, composition, protein concentration, concentration of nitrogen-containing species, nitrogen concentration, carbohydrate concentration, lipid (e.g. fat) concentration, fatty acid (i.e. volatile fatty acid, for example acetic acid) concentration, and/or pH of material (e.g. organic matter and/or organic matter slurry comprising organic matter and water) in the first and/or second chambers. The method may comprise the controller receiving the measurements of the said one or more parameters. The method may comprise the controller transferring a portion (e.g. repeatedly transferring portions) of the organic matter between the first and second chambers responsive to received measurements of the volume, mass, composition, protein concentration, concentration of nitrogen-containing species, nitrogen concentration, carbohydrate concentration, lipid (e.g. fat) concentration, fatty acid (i.e. volatile fatty acid, for example acetic acid) concentration, and/or pH of material (e.g. organic matter and/or organic matter slurry comprising organic matter and water) in the first and/or second chambers.

The method may comprise adding one or more hydrolytic enzymes to the first chamber responsive to (e.g. dependent on, for example in proportion to) the protein concentration and/or nitrogen concentration measured in the first chamber. That is to say, the amount of hydrolytic enzymes added to the first chamber typically depends on the measured protein concentration and/or nitrogen concentration.

The method may comprise adding water to the first chamber if the nitrogen concentration measured in said first chamber exceeds a threshold (e.g. exceeds a concentration of 1000 mg/L). The method may comprise adding water to the second chamber if the nitrogen concentration measured in said second chamber exceeds a threshold (e.g. exceeds a concentration of 1000 mg/L).

The method may comprise adding water to the second chamber if the volatile fatty acid concentration (e.g. the acetate concentration) measured in said second chamber exceeds a threshold (e.g. exceeds a concentration of 300 mg/L).

The method may comprise transferring a portion of the organic matter in the first chamber from said first chamber to the second chamber, wherein the volume of the portion of organic matter transferred is determined, taking into account the volatile fatty acid concentration (e.g. the acetate concentration) measured in the first chamber, so that the volatile fatty acid concentration (e.g. the acetate concentration) in the second chamber does not exceed a threshold (e.g. a concentration of 300 mg/L).

The method may comprise adding water to the second chamber if the volatile fatty acid concentration (e.g. the acetate concentration) measured in said second chamber exceeds a threshold (e.g. exceeds a concentration of 300 mg/L) before (e.g. immediately before) transferring a portion of the organic matter in the first chamber from said first chamber to the second chamber.

The method may comprise repeatedly transferring portions of the organic matter in the first chamber from said first chamber to the second chamber. The volume of each portion of organic matter transferred from the first chamber to the second chamber is typically determined taking into account the volatile fatty acid concentration (e.g. the acetate concentration) measured in the first chamber and the volume of organic matter in the first chamber (i.e. the volume of organic matter in the first chamber immediately before the portion of organic matter is transferred).

The method may comprise repeatedly, within one working cycle of the apparatus, transferring portions of the organic matter in the first chamber from the first chamber to the second chamber. One working cycle typically includes a period of time during which organic matter is added to the apparatus (i.e. through the inlet) and a (i.e. non-overlapping) period of time during which organic matter is digested in the first and/or second chambers. One working cycle may last 24 hours.

At the beginning of each working cycle, the first chamber typically retains a maximum volume of organic matter. At the end of each working cycle, the first chamber typically retains a minimum volume of organic matter (for example approximately no organic matter). The method may comprise varying the rate of transfer of organic matter from the first chamber to the second chamber. The rate of transfer of organic matter from the first chamber to the second chamber may be determined taking into account the volatile fatty acid concentration (e.g. the acetate concentration) measured in the first chamber (and e.g. the volume of organic matter in the first chamber at the beginning of the working cycle (e.g. the maximum volume of organic matter in the first chamber)). Varying the rate of transfer of organic matter from the first chamber to the second chamber may comprise varying the time between transfers of portions of organic matter from the first chamber to the second chamber and/or varying the volume of the portions of organic matter transferred. The method may comprise repeatedly, within one working cycle of the apparatus, transferring portions of the organic matter in the first chamber from the first chamber to the second chamber, the volume of each portion of organic matter transferred from the first chamber to the second chamber being determined taking into account the volatile fatty acid concentration (e.g. the acetate concentration) measured in the first chamber, the volume of organic matter in the first chamber at the beginning of the working cycle (e.g. the maximum volume of organic matter in the first chamber), and the volume of organic matter in the first chamber immediately before the portion of organic matter is transferred. The volume of each portion of organic matter transferred from the first chamber to the second chamber is typically determined also taking into account a target volume of organic matter which should remain in the first chamber at the end of the working cycle (for example approximately zero volume of organic matter in the first chamber) and/or a target number of transfers of organic matter from the first chamber to the second chamber which should take place before the end of the working cycle.

The method may comprise transferring organic matter from the second chamber into the first chamber if the volatile fatty acid concentration (e.g. the acetate concentration) measured in the second chamber exceeds a threshold (e.g. exceeds a concentration of 300 mg/L).

The method may comprise transferring organic matter from the second chamber into the first chamber if the volume of material in the second chamber exceeds a threshold. The method may comprise the gas purifier filtering one or more gases produced during anaerobic digestion of organic matter in the first and/or second chambers. The method may comprise the gas purifier (e.g. selectively) removing one or more of carbon dioxide ($CO_2$), hydrogen sulphide ($H_2S$) and/or ammonia ($NH_3$) from the gases.

The acetogenic microorganisms may comprise (e.g. consist of) acetogenic bacteria. The acetogenic microorganisms may comprise (e.g. consist of) acetogenic bacteria belonging to the genus *Acetobacterium*. The acetogenic microorganisms may comprise (e.g. consist of) acetogenic bacteria belonging to the species *Acetobacterium woodii*.

The acetogenic microorganisms may also be acidogenic microorganisms. The acetogenic bacteria may also be acidogenic. The acetogenic bacteria belonging to the genus *Acetobacterium* may also be acidogenic. Acetogenic bacteria belonging to the species *Acetobacterium woodii* are typically also acidogenic.

The methanogenic microorganisms may comprise (e.g. consist of) methanogenic archaea. The methanogenic microorganisms may comprise (e.g. consist of) methanogenic archaea belonging to the genus *Methanosaeta*. The methanogenic microorganisms may comprise (e.g. consist of) methanogenic archaea belonging to the species *Methanosaeta concilii*.

A third aspect of the invention provides a method for generating heat and/or electricity, the method comprising: carrying out the steps of the second aspect of the invention; and generating electricity by combusting methane produced by anaerobic digestion of the organic matter in the first and/or second chambers.

A fourth aspect of the invention comprises a method of generating methane (e.g. biogas comprising methane) from organic matter, the method comprising: exposing the organic matter to acetogenic microorganisms at a temperature equal to or below 10° C.; and subsequently exposing at least a portion of the organic matter to methanogenic microorganisms at a temperature greater than 10° C.

The method may comprise the step of macerating (e.g. chopping up) the organic matter. The step of macerating the organic matter typically occurs prior to exposing the organic matter to acetogenic microorganisms. The method may comprise the step of adding water to the organic matter (for example, mixing the organic matter with water). Water may be added to the organic matter during the maceration step and/or after maceration.

The method may comprise exposing the organic matter to acetogenic microorganisms at a temperature equal to or below 8° C., or equal to or below 6° C., or equal to or below 4° C.

The method may comprise exposing the at least a portion of the organic matter to methanogenic microorganisms at a temperature greater than 15° C., or greater than 20° C., or greater than 25° C., or greater than 30° C.

The method may comprise agitating (e.g. mixing) the organic matter (e.g. a slurry of organic matter and water) during exposure to the acetogenic bacteria. The method may comprise agitating (e.g. mixing) the organic matter (e.g. a slurry of organic matter and water) during exposure to the methanogenic archaea.

The method may comprise exposing the organic matter to one or more hydrolytic enzymes (i.e. hydrolases). The one or more hydrolytic enzymes may comprise one or more of the following: amylases, proteases, lipases, cellulases. The step of exposing the organic matter to one or more hydrolytic enzymes may take place before and/or during the step of exposing the organic matter to acetogenic microorganisms at a temperature equal to or below 10° C.

The method may comprise exposing the organic matter to both acetogenic microorganisms and methanogenic microorganisms at a temperature equal to or below 10° C.; and subsequently exposing at least a portion of the organic matter to both the acetogenic microorganisms and the methanogenic microorganisms at a temperature greater than 10° C. The acetogenic microorganisms tend to proliferate at temperatures equal to or below 10° C. while the methanogenic microorganisms tend be inhibited at temperatures equal to or below 10° C. The methanogenic microorganisms tend to proliferate at temperatures greater than 10° C.

The method may comprise first exposing the organic matter to both acetogenic microorganisms and methanogenic microorganisms at a temperature equal to or below 10° C.; second, exposing a first portion of the organic matter to both the acetogenic microorganisms and the methanogenic microorganisms at a temperature greater than 10° C.; and third, exposing a second portion of the organic matter to both the acetogenic microorganisms and the methanogenic microorganisms at a temperature greater than 10° C. The method may comprise sequentially exposing three or more portions of the organic matter to both the acetogenic microorganisms and the methanogenic microorganisms at a temperature greater than 10° C.

The method may comprise repeatedly (e.g. cyclically) varying the temperature of at least a portion of the organic matter, during exposure to both acetogenic and methanogenic microorganisms, between temperatures equal to or less than 10° C. and temperatures greater than 10° C. The method may comprise repeatedly (e.g. cyclically) moving at least a portion of the organic matter, during exposure to both acetogenic and methanogenic microorganisms, between at least first and second locations (e.g. containers), wherein the first location is held at (e.g. refrigerated to) a temperature equal to or less than 10° C. and the second location is held at (e.g. heated to) a temperature greater than 10° C.

The method may comprise determining (e.g. measuring) one or more parameters indicative of volume, mass, composition, protein concentration, concentration of nitrogen-containing species, nitrogen concentration, carbohydrate concentration, lipid (e.g. fat) concentration, fatty acid (i.e. volatile fatty acid, for example acetic acid) concentration, and/or pH of the organic matter. The method may comprise varying the temperature of the organic matter responsive to the determined (e.g. measured) one or more parameters.

The method may comprise exposing the organic matter to hydrolytic enzymes, the amount of hydrolytic enzymes to which the organic matter is exposed being dependent on (e.g. in proportion to) the measured protein concentration and/or the measured nitrogen concentration.

The method may comprise purifying (e.g. filtering) one or gases produced on anaerobic digestion of organic matter. The method may comprise (e.g. selectively) removing one or more of carbon dioxide ($CO_2$), hydrogen sulphide ($H_2S$) and/or ammonia ($NH_3$) from the gases.

The acetogenic microorganisms may comprise (e.g. consist of) acetogenic bacteria. The acetogenic microorganisms may comprise (e.g. consist of) acetogenic bacteria belonging to the genus *Acetobacterium*. The acetogenic microorganisms may comprise (e.g. consist of) acetogenic bacteria belonging to the species *Acetobacterium woodii*.

The acetogenic microorganisms may also be acidogenic microorganisms. The acetogenic bacteria may also be acidogenic. The acetogenic bacteria belonging to the genus *Acetobacterium* may also be acidogenic. Acetogenic bacteria belonging to the species *Acetobacterium woodii* are typically also acidogenic.

The methanogenic microorganisms may comprise (e.g. consist of) methanogenic archaea. The methanogenic microorganisms may comprise (e.g. consist of) methanogenic archaea belonging to the genus *Methanosaeta*. The methanogenic microorganisms may comprise (e.g. consist of) methanogenic archaea belonging to the species *Methanosaeta concilii*.

A fifth aspect of the invention provides a method of hydrolysing organic matter, the method comprising: determining (e.g. measuring) a parameter indicative of the amount (e.g. concentration) of protein in the organic matter; and exposing the organic matter to one or more hydrolytic enzymes, wherein the quantity of hydrolytic enzymes to which the organic matter is exposed is dependent on the value of the determined (e.g. measured) parameter.

Organic matter typically comprises proteins, carbohydrates, lipids and lignocellulose, as well as other substances. Different hydrolytic enzymes are capable of catalysing the hydrolysis of different constituent macromolecules. For example, an amylase is capable of catalysing the hydrolysis of starch (a carbohydrate) into simple sugars. A protease is capable of catalysing the hydrolysis of peptide bonds in proteins to form amino acids. A cellulase is capable of catalysing the hydrolysis of cellulose and related polysaccharides. A lipase is capable of catalysing the hydrolysis of lipids to form fatty acids.

The quantity of hydrolytic enzymes to which the organic matter is exposed is typically in proportion to the value of the determined (e.g. measured) parameter.

A sixth aspect of the invention provides a microbiological culture for use in anaerobic digestion of organic matter, the microbiological culture comprising (e.g. or consisting of) one or more bacteria belonging to the genus *Acetobacterium*.

The one or more bacteria present in the culture typically comprise (e.g. or consist of) acetogenic bacteria belonging to the genus *Acetobacterium*. The acetogenic bacteria are typically homoacetogenic, for example homoacetogenic *Acetobacterium woodii*.

Thus, the one or more acetogenic bacteria may comprise (e.g. or consist of) the bacteria belonging to the species *Acetobacterium woodii*.

The acetogenic bacteria are typically also acidogenic bacteria.

The microbiological culture may comprise predominantly acetogenic bacteria belonging to the genus *Acetobacterium*. The microbiological culture may comprise predominantly bacteria belonging to the genus *Acetobacterium woodii*.

However, the microbiological culture may further comprise one or more archaea belonging to the genus *Methanosaeta*. The one or more archaea are typically methanogenic archaea belonging to the genus *Methanosaeta*. The one or more archae may have acetate as their predominant or sole substrate for methanogenesis. The one or more archaea present in the culture may comprise (e.g. or consist of) archaea belonging to the species *Methanosaeta concilii*.

The microbiological culture may comprise predominantly bacteria belonging to the genus *Acetobacterium* and archaea belonging to the genus *Methanosaeta*. The microbiological culture may comprise predominantly bacteria belonging to the species *Acetobacterium woodii*; and archaea belonging to the species *Methanosaeta*.

A seventh aspect of the invention provides a microbiological culture for use in anaerobic digestion of organic matter, the microbiological culture comprising (e.g. or consisting of) one or more archaea belonging to the genus *Methanosaeta*.

The one or more archaea are typically methanogenic archaea belonging to the genus *Methanosaeta*. The one or more archaea may belong to the species *Methanosaeta concilii*.

The microbiological culture may comprise predominantly archaea belonging to the genus *Methanosaeta*. The microbiological culture may comprise predominantly archaea belonging to the genus *Methanosaeta concilii*. It may be that the methanogenic archae present in the microbiological culture consist of archaea belonging to the genus *Methanosaeta*. It may be that the methanogenic archae present in the microbiological culture consist of archaea belonging to the species *Methanosaeta concilii*.

The microbiological culture may comprise one or more bacteria belonging to the genus *Acetobacterium*. The one or more bacteria are typically acetogenic bacteria belonging to the genus *Acetobacterium*. The one or more bacteria may belong to the species *Acetobacterium woodii*. The one or more bacteria are typically also acidogenic.

The microbiological culture may comprise predominantly bacteria belonging to the genus *Acetobacterium* and archaea belonging to the genus *Methanosaeta*. The microbiological culture may comprise predominantly bacteria belonging to the species *Acetobacterium woodii* and archaea belonging to the species *Methanosaeta concilii*.

The microbiological culture of the sixth or seventh aspects may include no bacteria other than *Acetobacterium* (typically no bacteria other than *Acetobacterium* wood/i).

The microbiological culture of the sixth or seventh aspects may include no archaea other than *Methanosaeta* (typically no archaea other than *Methanosaeta concilii*).

An eighth aspect of the invention provides a method of generating methane (e.g. biogas comprising methane) from organic matter, the method comprising exposing the organic matter to bacteria belonging to the genus *Acetobacterium* and archaea belonging to the genus *Methanosaeta*, for example exposing the organic matter to a microbiological culture according to the sixth or seventh aspects comprising both *Acetobacterium* and *Methanosaeta*

The bacteria may belong to the species *Acetobacterium woodii*. The archaea may belong to the species *Methanosaeta concilii*.

The method may comprise exposing the organic matter to bacteria belonging to the genus *Acetobacterium* (e.g. belonging to the species *Acetobacterium* wood/i) at a temperature equal to or below 10° C., or equal to or below 8° C., or equal to or below 6° C., or equal to or below 4° C.

The method may comprise exposing the organic matter to archaea belonging to the genus *Methanosaeta* (e.g. belonging to the species *Methanosaeta concilii*) at a temperature greater than 10° C., or greater than 8° C., or greater than 6° C., or greater than 4° C.

The method may comprise exposing the organic matter to the bacteria belonging to the genus *Acetobacterium* (e.g. belonging to the species *Acetobacterium woodii*) at a temperature equal to or below 10° C. and subsequently exposing at least a portion of the organic matter to the archaea belonging to the genus *Methanosaeta* (e.g. belonging to the species *Methanosaeta concilii*) at a temperature greater than 10° C.

The method may comprise exposing the organic matter to both the bacteria belonging to the genus *Acetobacterium* (e.g. belonging to the species *Acetobacterium woodii*) and archaea belonging to the genus *Methanosaeta* (e.g. belonging to the species *Methanosaeta concilii*) at a temperature equal to or below 10° C.; and subsequently exposing at least a portion of the organic matter to both the bacteria belonging to the genus *Acetobacterium* (e.g. belonging to the species *Acetobacterium woodii*) and archaea belonging to the genus *Methanosaeta* (e.g. belonging to the species *Methanosaeta concilii*) at a temperature greater than 10° C.

The method may also comprise exposing the organic material to one or more hydrolytic enzymes. The one or more hydrolytic enzymes are typically provided from a source which does not include microorganisms, for example from a powdered (e.g. lyophilised) enzyme preparation, or an enzyme solution, which does not include microorganisms.

It may be that at least one chemical species in the organic matter, or at least 0.1% by mass of the organic matter, is hydrolysed into a form which can be and is metabolised by *Acetobacterium* (e.g. *Acetobacterium woodii*) due to the presence of the one or more said hydrolytic enzymes and not by bacterial digestion (i.e. bacterial hydrolysis).

A ninth aspect of the invention provides a kitchen having therein the apparatus according to the first aspect of the invention. The kitchen may be a domestic or commercial kitchen comprising a cooker. It may be that the apparatus retains organic matter, which may be food waste. It may be that the organic matter is located in the first and/or second chambers. It may be that the apparatus comprises acetogenic microorganisms. The acetogenic microorganisms may also be acidogenic microorganisms. It may be that the apparatus comprises methanogenic microorganisms. It may be that the apparatus comprises a microbiological culture according to the sixth or seventh aspects of the invention. It may be that the first chamber is refrigerated (e.g. to a temperature equal to or below 10° C., or equal to or below 8° C., or equal to or below 6° C., or equal to or below 4° C.). It may be that the second chamber is heated (e.g. to a temperature greater than 10° C., or greater than 15° C., or greater than 20° C., or greater than 25° C., or greater than 30° C.). Optional and preferred features of any one aspect of the invention may be features of any other aspect of the invention.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
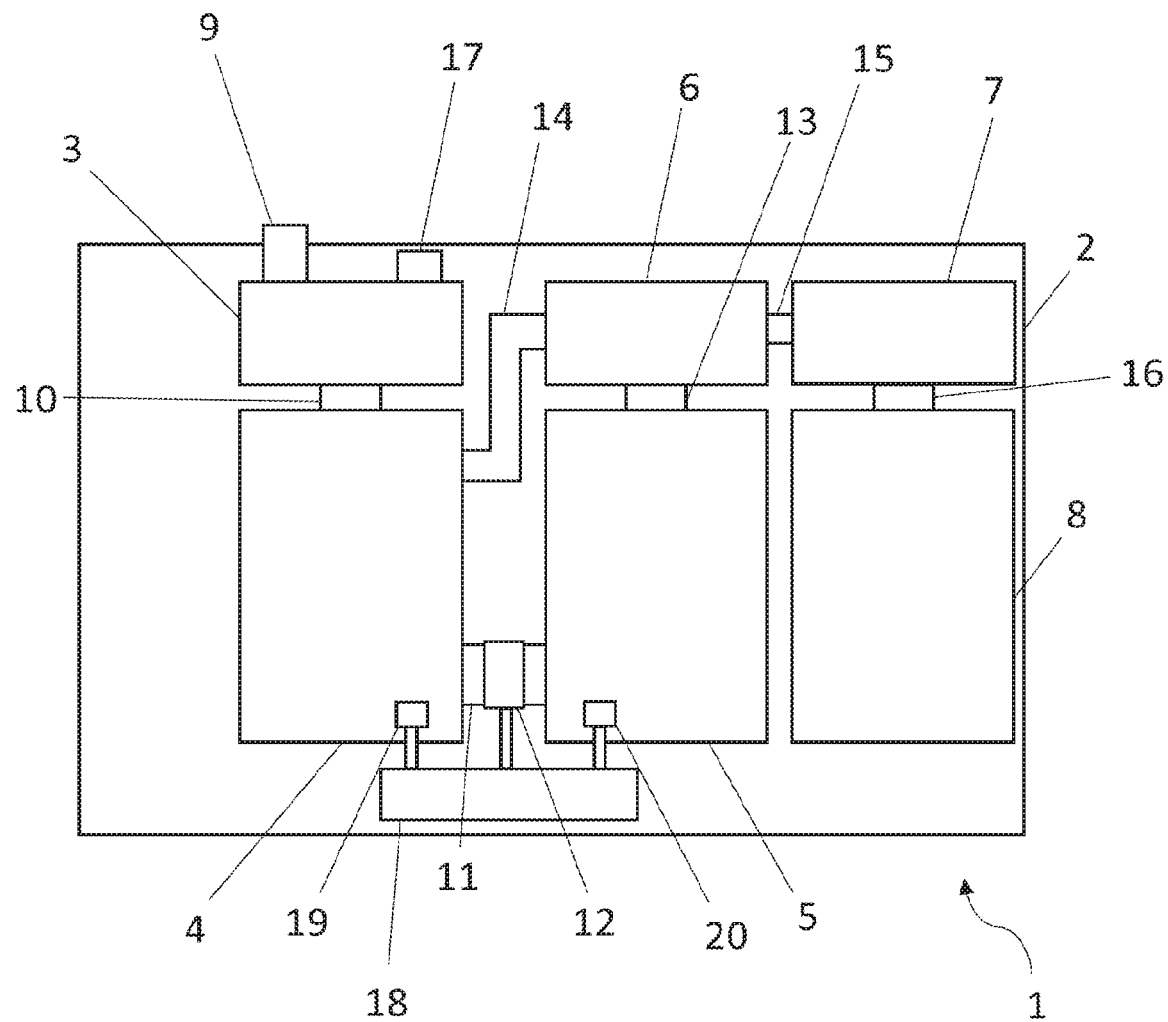
FIG. 1 shows a schematic plan of a first example of an anaerobic digestion apparatus.
Figure 2:
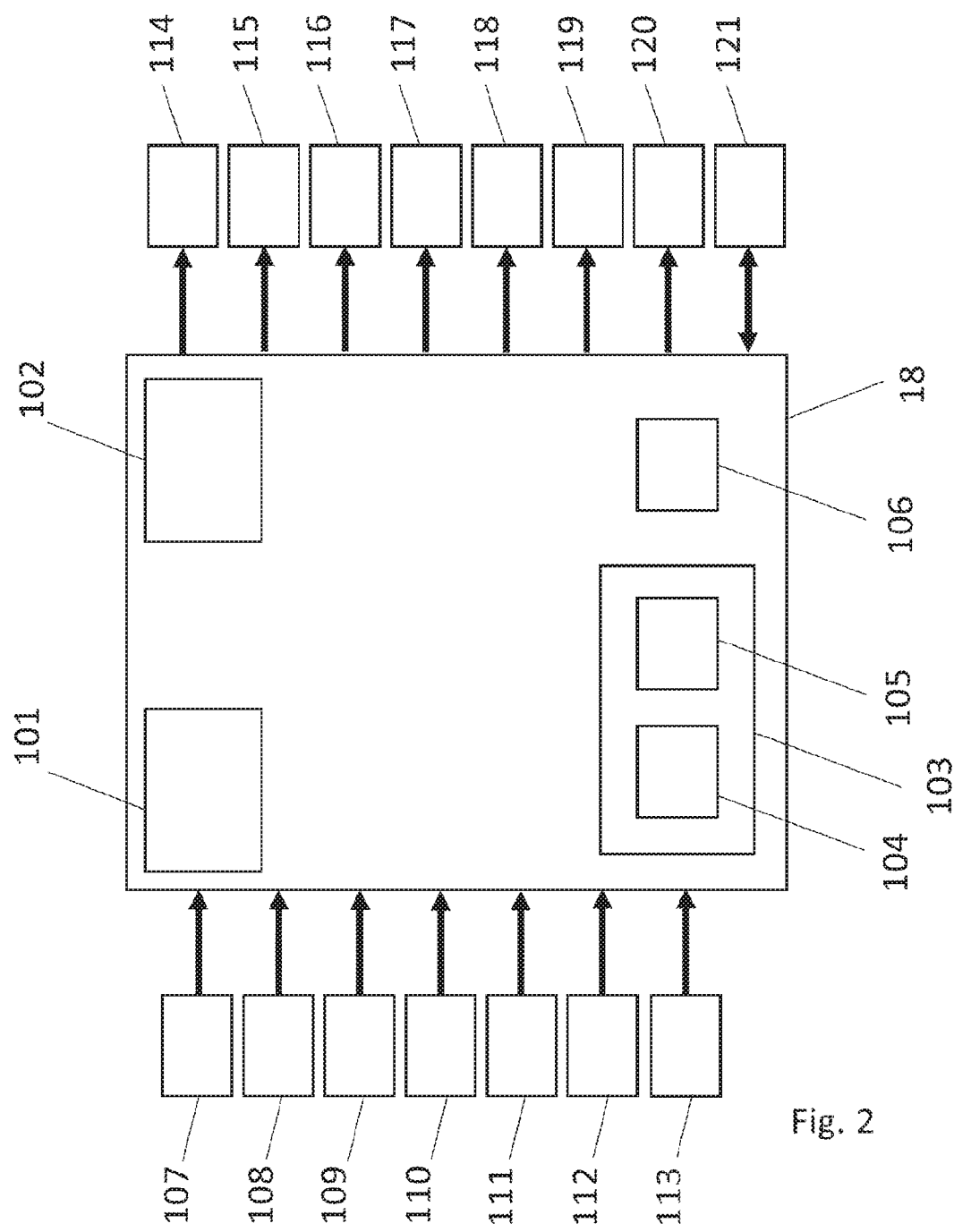
FIG. 2 shows the inputs and outputs of a controller which forms part of the apparatus of FIG. 1.

A first example of anaerobic digestion apparatus 1, for generating electricity by the combustion of biogas produced on anaerobic digestion of waste food matter, is illustrated schematically in FIG. 1. The apparatus comprises an external housing 2 which contains a maceration chamber 3, a first digestion chamber 4, a second digestion chamber 5, a gas purification chamber 6, a gas accumulator 7 and a gas converter 8. A sealable inlet 9 for receiving waste food matter extends through the housing 2 into the maceration chamber 3. The maceration chamber 3 is connected to the first digestion chamber 4 through a first sealable pipe 10. The first digestion chamber 4 is connected to the second digestion chamber 5 through a second sealable pipe 11 by way of a pump 12. The second digestion chamber 5 is connected to the gas purification chamber 6 by way of a third sealable pipe 13. The pipe 13 is fitted with a pressure check valve (not shown). The first digestion chamber 4 is also connected to the gas purification chamber 6 by way of a fourth sealable pipe 14. The gas purification chamber 6 is connected to the gas accumulator 7 by way of a fifth sealable pipe 15. The gas accumulator 7 is connected to the gas converter 8 by way of a fourth sealable pipe 16. The maceration chamber is provided with a water source 17. The apparatus also comprises a controller 18 in communication with first digestion chamber sensing apparatus 19 and second digestion chamber sensing apparatus 20. The controller 18 is also coupled to the pump 11.

The maceration chamber 3 houses a macerator (not shown). The macerator typically has one or more perforated cutting plates. The macerator is located below the inlet 9 such that waste food matter entering the apparatus through the inlet passes through the macerator. The water source 17 typically comprises one or more water jets configured to direct pressurised water onto the perforated cutting plates of the macerator.

The first digestion chamber 4 is located below the maceration chamber. The first digestion chamber 4 is refrigerated in use (for example by way of a heat pump) to a temperature of approximately 4° C. The temperature of the first digestion chamber 4 is thermostatically controlled by the controller. The first digestion chamber houses one or more rotatable paddles (not shown) for mixing any contents contained therein. The first digestion chamber is provided with hydrolytic enzymes, typically including an amylase, a protease, a lipase and a cellulase. The particular enzymes present in the first digestion chamber can be customised dependent on the composition of the food waste matter to be digested. Enzymes may be provided in the form of lyophilised enzymes, for example in solid form (e.g. a tablet of lyophilised enzymes) or dispersed in a liquid diluent. The enzymes may be stored in a refrigerated region adjacent to the first digestion chamber.

The second digestion chamber 5 is heated (for example by way of heating elements) in use to a temperature of approximately 35° C. The temperature of the second digestion chamber 5 is thermostatically controlled. The second digestion chamber is provided with a microbiological inoculum containing bacteria belonging to the genus *Acetobacterium* (and in particular the species *Acetobacterium woodii* (as deposited at the Leibniz-Institut DSMZ-Deutsche Sammlung von Mikroorganismen und Zellkulturen GmbH under deposit number DSM 1030 and at the American Type Culture Collection under deposit number ATCC 29683)) and archaea belonging to the genus *Methanosaeta* (and in particular the species *Methanosaeta concilii* (as deposited at the Leibniz-Institut DSMZ-Deutsche Sammlung von Mikroorganismen und Zellkulturen GmbH under deposit number DSM 3671 and at the American Type Culture Collection under deposit number ATCC 35969)).

The pump 12 is a two-way pump, meaning that material may be pumped either from the first digestion chamber into the second digestion chamber, or from the second digestion chamber into the first digestion chamber, through the pipe 11. Alternatively, two separate pumps may be employed.

The controller 18 (as illustrated in more detail in FIG. 3) has a user interface 101 and an internet interface 102 for connecting with a remote device. The controller has a memory 103 which stores computer executable program code 104 as well as a database 105 storing device calibration parameters. The controller also has a clock 106. The controller is typically a programmable logic controller (PLC).

The controller is connected electronically to the first digestion chamber sensing apparatus 19 and the second digestion chamber sensing apparatus 20. The first and/or second digestion chamber sensing apparatuses typically include one or more temperature sensors 107, one or more volatile fatty acid (VFA) sensors (such as an acetate sensor) 108, one or more level sensors 109, one or more load cells 110, one or more nitrogen sensors 111, one or more pH sensors 112, and one or more volume sensors 113.

Each VFA sensor 108 typically combines a Fabry-Perot spectrometer with an Attenuated Total Reflection (ATR) probe which permits the concentration of VFAs in the first and/or second digestion chambers to be determined without removing samples of material from the respective chambers. A suitable VFA sensor would be the OPTI-VFA sensor developed as part of the European Commission Project *Novel monitoring and process control system for efficient production of VFA and biogas in anaerobic digestion plant* (Project ID: 606096) and discussed in detail in "*Validation and improvement of the OPTI-VFA sensor for online VFA monitoring*"; Zhe Deng, Master's thesis, *Delft University of Technology*, 2015, the contents of which are incorporated herein by virtue of this reference. The VFA sensors are typically configured to determine the concentration of acetate in the first and/or second digestion chambers. The VFA sensors may also be configured to determine the total VFA concentration in the first and/or second digestion chambers.

Each level sensor 109 is typically configured to measure the level of material in the first and/or second digestion chambers.

Each load cell 110 is typically configured to measure the weight of material in the first and/or second digestion chambers.

Each nitrogen sensor 111 is typically a Kjeldahl probe as is known in the art for sensing and determining the concentration of nitrogen and nitrogen-containing compounds in the contents of the first and/or second digestion chambers.

Each pH sensor 112 is typically configured to measure the pH of material in the first and/or second digestion chambers.

Each volume sensor 113 is typically configured to measure the volume of gas retained in the first and/or second digestion chambers.

The controller is programmed to receive inputs from the one or more temperature sensors 107, one or more volatile fatty acid (VFA) sensors (such as an acetate sensor) 108, one or more level sensors 109, one or more load cells 110, one or more nitrogen sensors 111, one or more pH sensors 112, and one or more volume sensors 113 and to carry out one or more device control actions dependent on the result of comparing the one or more inputs to the calibration parameters stored in the database 105. The possible device control actions include sealing and unsealing the inlet 114, dispensing enzymes into the first digestion chamber 115, operating the pump between the first and second digestion chambers 116, adjusting the temperature of the first digestion chamber 117, adjusting the temperature of the second digestion chamber 118, operating the mixing paddles in the first and second digestion chambers 119, operating the water sprays 120, and activating or deactivating the gas converter 121.

The stored calibration parameters typically include enzyme weighting parameters, threshold nitrogen concentrations for the first and/or second digestion chambers, target temperatures for the first and/or second digestion chambers, and threshold volatile fatty acid concentrations (and in particular threshold acetate concentrations) for the first and/or second digestion chambers.

The gas purifier 6 is provided above the second digestion chamber. The gas purifier 6 typically comprises a number of filters (e.g. activated charcoal and/or potassium permanganate filters) configured to trap carbon dioxide ($CO_2$), hydrogen sulphide ($H_2S$) and ammonia ($NH_3$). The gas purifier filters are configured to allow methane ($CH_4$) to pass unimpeded. The pipe 14 between the first digestion chamber and the gas purifier is typically sealed when the inlet 9 is unsealed and, vice versa, the pipe 14 is typically unsealed when the inlet 9 is sealed.

The gas accumulator 7 provides a chamber within which gas can be stored before it is pumped into the gas converter 8.

The gas converter 8 is typically a micro combined heat and power (micro-CHP) device as is known in the art. The micro-CHP device is configured to generate heat and electricity through the combustion of methane.

Apparatus components which typically come into contact with food matter or digestate during use are typically made of stainless steel, and in particular EN 1.4301/AISI 304 stainless steel. Apparatus components which typically come into contact with biogas liberated during anaerobic digestion are also typically made of stainless steel, and in particular EN 1.4571/AISI 316Ti stainless steel. Each component is typically designed to be removable and replaceable, such that components can also be reused.

Figure 3:
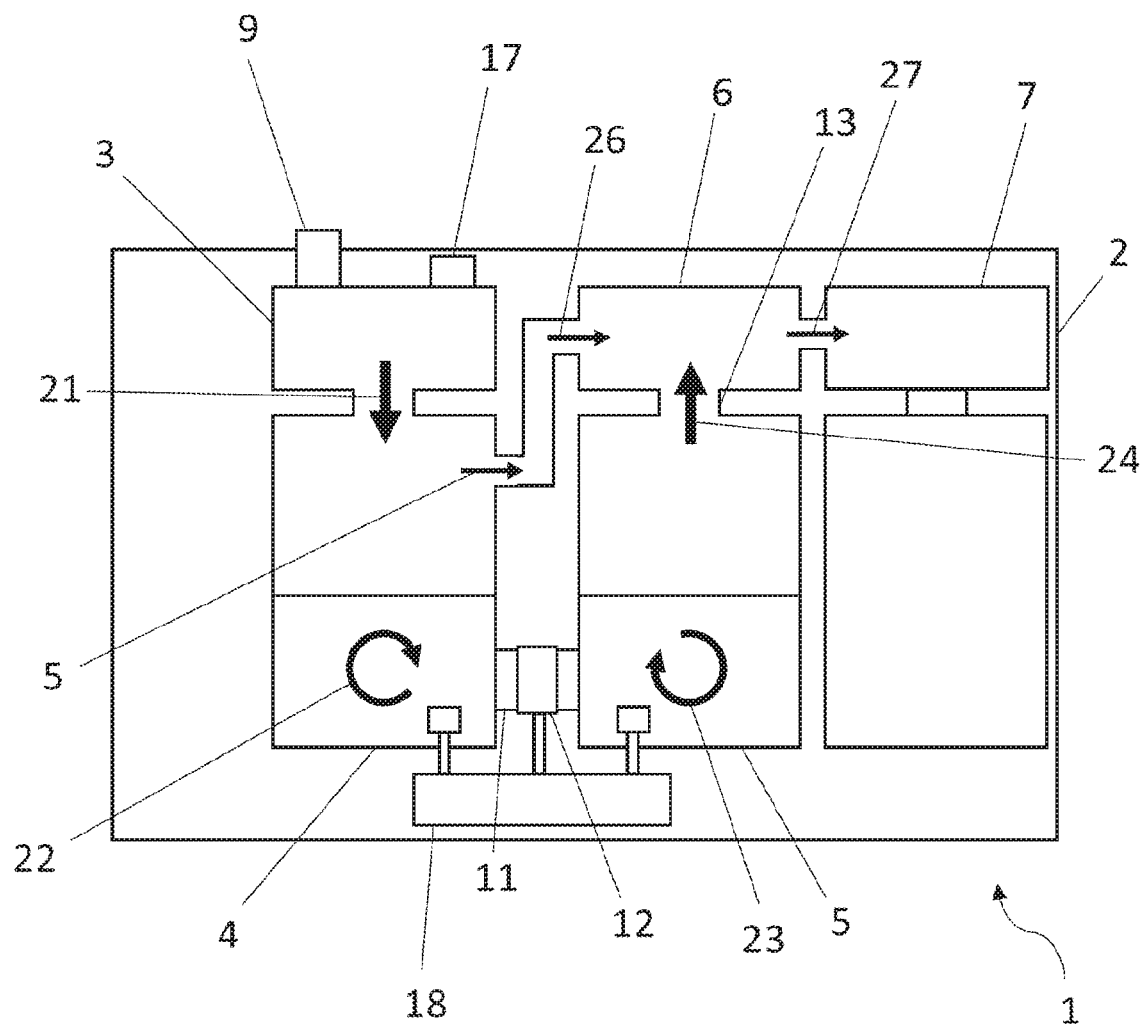
FIG. 3 shows schematically the movement of material through the anaerobic digestion apparatus of FIG. 1 in use.
Figure 4:
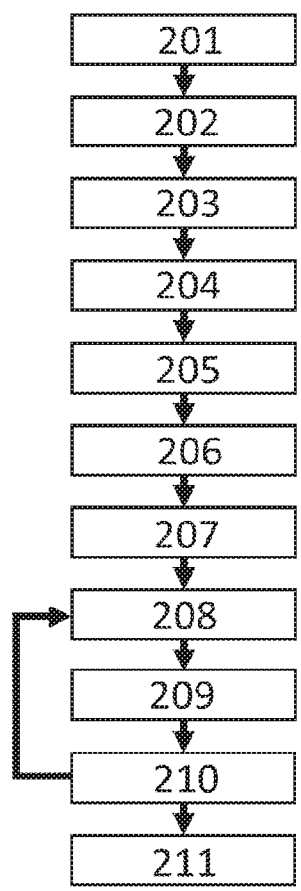
FIG. 4 is a flow chart of the anaerobic digestion steps taken over an example 24 hour period of operation of the anaerobic digestion apparatus.

The process for the generation of electricity through the anaerobic digestion of waste food matter is illustrated in FIGS. 3 and 4.

Waste food matter enters the maceration chamber through the inlet (step 201 in FIG. 4). When food matter enters the maceration chamber, the macerator is switched on and the food matter is cut down into small particles (having characteristic diameters of between 0.5 mm to 0.9 mm) by the perforated cutting plates of the macerator. Macerated food matter travels under gravity through pipe 10 into the first digestion chamber below the macerator (step 202), as indicated by arrow 21. Pressurised water directed by the water source 17 onto the cutting plates assists in pushing the macerated food matter into the first digestion chamber, while also cleaning the maceration chamber, reducing clogging and unpleasant smells. The macerated food matter and water forms a slurry which is contained within the first digestion chamber. Because the first digestion chamber is refrigerated, the metabolic activity of any microorganisms naturally present in the food matter is inhibited and so decomposition of the food matter slurry is discouraged, as is the production of further unpleasant smells.

When the controller determines that sufficient matter has been added to the storage tank (based on the outputs of the level sensor, the load cell or the volume sensor), or when an appropriate time has been reached (as determined using the clock), anaerobic digestion of the food matter may begin. At this point, the inlet is sealed (step 203) so that no further food matter may be added to the maceration chamber. The inlet seal is airtight such that no gases may escape through the inlet to the surrounding environment. Sealing the inlet also causes the pipe 14 between the first digestion chamber and the gas purifier to open.

The controller receives a measurement of the nitrogen concentration in the first digestion chamber as measured by the nitrogen sensor and introduces hydrolytic enzymes into the first digestion chamber in proportion to the nitrogen concentration (step 204) taking into account the enzyme weighting parameters stored in the database. The enzymes can be introduced into the first digestion chamber by a metred pump under the control of the controller.

The paddles within the storage chamber rotate (step 205), resulting in mixing of the food matter slurry (as indicated by arrow 22), ensuring thorough hydrolysis of the food matter slurry.

When the controller determines that a sufficient period of time has passed (typically based on the output of the clock) such that hydrolysis of the food matter slurry in the first digestion chamber is essentially complete, anaerobic digestion may then commence by the introduction of anaerobic microorganisms. A fresh culture of microorganisms may be introduced directly into the first digestion chamber by the controller. Indeed, this is what it is done on first starting the apparatus. However, in normal use, previously digested material mixed with microorganisms will already be present in the second digestion chamber. Accordingly, microorganisms are typically introduced into the first digestion chamber by pumping a portion of digestate from the second digestion chamber into the first digestion chamber (step 206). The quantity of digestate pumped into the first digestion chamber may depend on the volume of digestate already present in the second digestion chamber. For example, the controller may receive a measurement of the volume of digestate in the second digestion chamber from the volume or level sensor and may transfer any material present in the second digestion chamber above a threshold volume (e.g. 30 litres) which is stored in the database.

Methanogenic microorganisms such as *Methanosaeta concilii* are widely susceptible to temperature variations and, in particular, show markedly decreased metabolic activity at low temperatures (e.g. below approximately 10° C.). Accordingly, when the microbiological inoculum (either in the form of a fresh culture or as existing digestate) is added to the refrigerated first digestion chamber, the methanogenic microorganisms are inactivated. In contrast, acidogenic and acetogenic microorganisms such as *Acetobacterium woodii* proliferate at such lower temperatures. Acidogenesis and acetogenesis therefore occur within the first digestion chamber as the acidogenic and acetogenic microorganisms convert hydrolysis products (such as glucose and organic acids) into acetic acid (e.g. via the Wood-Ljungdahl pathway).

As hydrolysis, acidogenesis and acetogenesis progress and amino acids are broken down, nitrogen may be released into the first digestion chamber. The controller therefore continues to monitor the output from the nitrogen sensor in the first digestion chamber. The controller compares the nitrogen concentration measured by the nitrogen sensor to the threshold nitrogen concentration stored as a calibration parameter in the memory and, if the measured nitrogen concentration exceeds the threshold, the controller activates the water sprays to add water to the first chamber (step 207) until the measured nitrogen concentration falls below the threshold. A typical nitrogen concentration threshold is 1000 mg/L. Rotation of the paddles ensures that acetogenesis is even throughout the first digestion chamber.

Food matter slurry is subsequently exchanged between the first digestion chamber and the second digestion chamber. When the controller determines that a sufficient period of time has passed (typically based on the output of the clock), the controller calculates a volume of slurry which should be transferred from the first digestion chamber to the second digestion chamber in order to ensure that the acetate concentration in the second digestion chamber does not exceed a threshold acetate concentration stored in the database. In particular, the controller receives a measurement of the acetate concentration in the first digestion chamber as determined by the VFA sensor in the first digestion chamber and uses this concentration to determine the volume to be transferred. The controller may also receive and take into account a measurement of the acetate concentration in the second digestion chamber as determined by the VFA sensor in the second digestion and a measurement of the volume of material in the second digestion chamber as determined by the load, level or volume sensor in the second digestion chamber, or the controller may access a previous measurement of the acetate concentration and volume of material in the second digestion chamber stored in the memory, or the controller may estimate the acetate concentration and volume of material in the second digestion chamber using, for example, the known rate at which methanogenic microorganisms convert acetate to methane and the length of time since the previous introduction of acetate into the second digestion chamber as well as the previous volume of material introduced into the second digestion chamber. The controller typically determines the volume of slurry which contains an amount of acetate less than the amount of acetate required to raise the concentration of acetate in the second digestion chamber beyond the stored acetate concentration threshold and then transfers this volume of the slurry from the first digestion chamber into the second digestion chamber (step 208).

As a simple example of how the controller can determine the volume of material to transfer, a target second digestion chamber acetate concentration C (which is less than the threshold acetate concentration) can be achieved by a transferring a volume of slurry $V_T$ from the first digestion chamber to the second chamber which is given by:

$$V_T = \frac{(C_2 - C)}{(C - C_1)} V_2$$

where $C_1$ is the acetate concentration in the first digestion chamber, $C_2$ is the acetate concentration in the second digestion chamber and $V_2$ is the volume of material in the second digestion chamber before the volume of slurry is transferred, assuming that the total volume of material in the second digestion chamber after the transfer is given by the sum of the volume of material in said second digestion chamber before the transfer and the volume of material transferred.

A typical acetate concentration threshold is 300 mg/L, above which methanogenic microorganisms do not typically function efficiently.

Because the temperature of the second digestion chamber is higher, methanogenic microorganisms are typically already active in the second digestion chamber. In addition, the methanogenic microorganisms already present in the transferred slurry are reactivated on transfer into the second digestion chamber. Methanogenesis of the transferred slurry therefore proceeds in the second digestion chamber, whereby the methanogenic microorganisms convert acetic acid in the slurry into methane. Rotation of the paddles in the second digestion chamber ensures that methanogenesis is even, as indicated by arrow 23 (step 209).

This process is then repeated periodically. At each stage, when the controller determines that a sufficient period of time has passed (again based on the output of the clock) (step 210), the controller compares the acetate concentration measured by the VFA sensor in the first digestion chamber to the threshold acetate concentration stored in the database and transfers another portion of the slurry from the first digestion chamber into the second digestion chamber, the volume of slurry transferred being dependent on the measured acetate concentration. By monitoring the VFA concentration in the first digestion chamber and adjusting the volume of slurry transferred accordingly, the acetate concentration in the second digestion chamber can be maintained below the threshold concentration and so methanogenesis can be made more efficient.

This exchange of material from the first digestion chamber to the second digestion chamber is repeated until the controller determines that sufficient time has passed based on the output of the clock (step 210), at which point rotation of the paddles ceases and any remaining material in the first digestion chamber is pumped into the second digestion chamber (step 211). If the VFA (e.g. acetate) concentration of the remaining material in the first digestion chamber is high (e.g. above 300 mg/L), the controller may add water to the first digestion chamber to dilute the remaining material before transfer into the second digestion chamber. However, the controller may also be programmed to distribute the feeding of material into the second chamber throughout each working cycle in such a way that there is typically no material remaining in the first digestion chamber at the end of the cycle, or such that the VFA concentration will not be so high as to require further dilution.

During anaerobic digestion, gases liberated in the first and second digestion chambers pass up (as indicated by arrows 24, 25 and 26) through the gas purifier 6 where contaminants such as $CO_2$, $H_2S$ and $NH_3$ are removed. Purified gas is pumped (as indicated by arrow 27) into the gas accumulator 5 for storage. When the volume of gas in the gas accumulator reaches a threshold volume, the gas is pumped into the micro-CHP for combustion to generate heat and electricity.

The pressure check valve in the pipe 13 ensures that the gas pressure in the second digestion chamber remains constant during the anaerobic digestion process.

Because the controller is provided with a clock, it can be programmed to regulate the anaerobic digestion process to benefit from reduced electricity costs at certain times of day. For example, food matter can be added to the apparatus throughout the daytime while in the evening the controller seals the inlet and begins the anaerobic digestion process as outlined hereinabove. By periodically feeding material from the first digestion chamber into the second digestion chamber and by monitoring the nitrogen and/or acetate concentrations throughout the night, optimal conditions for methanogenesis may be maintained such that methane output is maximised. In the morning, the paddles cease rotating and the controller moves any remaining matter from the first chamber into the second chamber. The inlet is then unsealed. The first digestion chamber is then again ready to receive new waste food matter throughout the following day. The anaerobic digestion process also continues to proceed in the second digestion chamber during the day while the first digestion chamber is receiving new waste food matter.

The controller may determine the amount of material to be transferred from the first digestion chamber to the second digestion chamber at each stage in the process based on ongoing measurements of, for example, the nitrogen and/or acetate concentrations and the volumes of material in each of the first and second digestion chambers. Alternatively, the controller may be programmed to regulate the transfer of material between the digestion chambers based on a model of the anaerobic digestion process. This model, and consequently an algorithm with which the controller is programmed, may be developed by carrying out a series of experiments in which the nitrogen and acetate concentrations and the second digestion chamber feeding rates are varied while the methane output from the digester is monitored. The data collected during the experiments can be modelled using artificial intelligence modelling methods (for example using fuzzy logic (e.g. Mamdani fuzzy logic) or a neural network (with e.g. Bayesian regularisation)) which would be familiar to the person skilled in the art. The model thus developed can be programmed using standard mathematical modelling software such as MATLAB®.

The volume of liquid and/or solid digestate in the second chamber may slowly rise over several days or weeks of use. Accordingly, it may be necessary to remove the second chamber periodically to remove digestate and to introduce fresh inoculum into the apparatus.

The controller may be configured to notify a user by way of the user interface (for example, by sounding an alarm or activating a warning light) if the nitrogen concentration and/or the VFA concentration exceeds a critical threshold value. Additionally or alternatively, the controller may be configured to notify a user by way of the user interface (for example, by sounding an alarm or activating a warning light) if the volume of digestate in the second digestion chamber exceeds a critical value (indicating that the second chamber should be emptied and the contents replaced with a fresh microbiological inoculum).

The apparatus may also be provided with one or more gas sensors configured to measure the concentration of methane outside the apparatus (i.e. in the surrounding atmosphere). The controller may be configured to notify a user by way of the user interface (for example, by sounding an alarm or activating a warning light) if the one or more sensors detect methane outside the apparatus (indicating that there is a gas leak).

The apparatus can be programmed to send and receive signals to and from a remote device by way of the internet interface (although other connectivity options are possible, such as the apparatus including one or more transmitters and receivers for Bluetooth communication). The remote device may be a personal computer, a tablet computer or a mobile telephone. A user may be able to monitor the status of the apparatus using the remote device. The controller can be programmed to send an alert to the remote device, for example, if the nitrogen concentration and/or the VFA concentration exceeds a critical threshold value, or if the volume of digestate in the second digestion chamber exceeds a critical value, or if the one or more gas sensors detect methane outside the apparatus.

The controller may also be configured to reduce the temperature of the second digestion chamber if the one or more gas sensors detect methane outside the apparatus (indicating that there is a gas leak). Cooling the second digestion chamber inhibits the anaerobic digestion process and reduces the production of methane. The controller may also be configured to reduce the temperature of the second digestion chamber if the nitrogen concentration and/or the VFA concentration exceeds a critical threshold value, or if the volume of digestate in the second digestion chamber exceeds a critical value, indicating that the system is excessively perturbed.

The skilled person will appreciate that various different hydrolytic enzymes may be used in the first digestion chamber. However, alpha-amylase may be preferable to other amylases since it is able to catalyse hydrolysis of starch quickly, at random locations along the starch chains. In any case, hydrolytic enzymes are generally safe for use in commercial or domestic applications (unlike the pathogenic species of hydrolytic microorganisms which are typically used in large-scale anaerobic digestion facilities). Enzymes speed up hydrolysis of the food matter significantly, which is important as hydrolysis is typically the rate limiting step in most anaerobic digestion processes. Typically around 99% of the hydrolysis which occurs in the first digestion chamber is enzymatic.

While it would, at least in theory, be possible to determine the concentration of various carbohydrates, celluloses, proteins and lipids in the food matter slurry (using, for example, gas chromatographic techniques) in the first digestion chamber in order to tailor the relative ratios of the various hydrolytic enzymes added by the controller, the inventor has found that it is sufficient to monitor the nitrogen concentration only. Assuming that dietary carbohydrates and fats do not contain nitrogen, almost all nitrogen present in the average diet is found in amino acid residues in proteins and so the total nitrogen concentration of the slurry provides a good indication of the total protein concentration. Indeed, the total protein concentration is typically estimated by multiplying the measured total nitrogen concentration by a factor of 6.25. Studies (see, for example, *Synthesis of Food Waste Compositional Data* 2012*and On-site treatment of organic waste from the public and hospitality sectors*, SKM Enviros and Frith Resource Management, both published by The Waste and Resources Action Programme (WRAP))

have found that the average ratio of carbohydrates to lipids to proteins in food waste matter analysed in the UK is 156:59.3:44.3. The concentration of carbohydrates and lipids in the food matter slurry can therefore be estimated by determining the concentration of protein in the slurry and applying the same or a similar empirical ratio (for example a ratio of 3:1:1). Appropriate hydrolytic enzymes (such as amylases, lipases and proteases) may be added to the slurry in the same ratio. In any case, protein hydrolysis is typically slower than hydrolysis of other food components and so determining the protein concentration is generally most important.

The method may comprise moving organic matter back from the second chamber to the first chamber. This provides a supply of new microorganisms in the first chamber for further anaerobic digestion.

The apparatus described hereinabove makes use of a microbiological inoculum containing *Acetobacterium woodii*; and *Methanosaeta concilii*. The skilled person will understand that the apparatus may be used with different microorganisms. Nevertheless, the inventor has found that an inoculum containing bacteria in the genus *Acetobacterium* and archaea in the genus *Methanosaeta* is particularly effective.

*Acetobacterium woodii* is preferred because it is a non-pathogenic, acidogenic and acetogenic bacterium which produces predominantly acetates (i.e. acetic acid or acetic acid salts) as a by-product of anaerobic digestion (as described in, for example, *Acetobacterium*, a *New Genus of Hydrogen-Oxidizing Carbon Dioxide-Reducing Anaerobic Bacteria*, W. E. Bach, S. Schoberth, R. S. Tanner and R. S. Wolfe, International Journal of Systematic Bacteriology, October 1977, Vol. 27, No. 4, p. 355-361). Under certain circumstances, *Acetobacterium woodii* can also produce succinate (i.e. succinic acid salts) as a by-product of anaerobic digestion. Other acetogenic bacteria are known to produce unwanted by-products (such as ethanol, butanol, butyrate and formate) in significant quantities.

*Methanosaeta concilii* is preferred because it is a non-pathogenic, methanogenic archaeon which digests acetic acid to produce methane.

The use of a combination of *Acetobacterium woodii* and *Methanosaeta concilii*, with no other microorganisms present to any significant extent, leads to an anaerobic digestive process with maximised methane output. The production of corrosive gases such as ammonia, hydrogen sulphide and carbon dioxide is also significantly reduced by using the combination of *Acetobacterium woodii*; and *Methanosaeta concilii*, which prolongs the useful lifetime of the apparatus components and increases the calorific value of the biogas produced meaning that fewer gas cleaning steps are required. Any succinate produced as a by-product of anaerobic digestion can be extracted from the left-over digestate, succinates being high-value substances having medical applications such as in the preparation of topical treatments for arthritis.

The inventor has also found that both *Acetobacterium woodii* and *Methanosaeta concilii* are particularly resilient microorganisms which are able to withstand significant perturbations in digester parameters (such as fluctuations in the concentrations of food waste matter components, nitrogen concentrations and volatile fatty acid (VFA) concentrations). These microorganisms are non-pathogenic and can be usefully combined with hydrolytic enzymes to provide an efficient anaerobic digester, overcoming the prejudice in the art that anaerobic digesters require the use of at least some pathogenic microorganisms.

Figure 5:
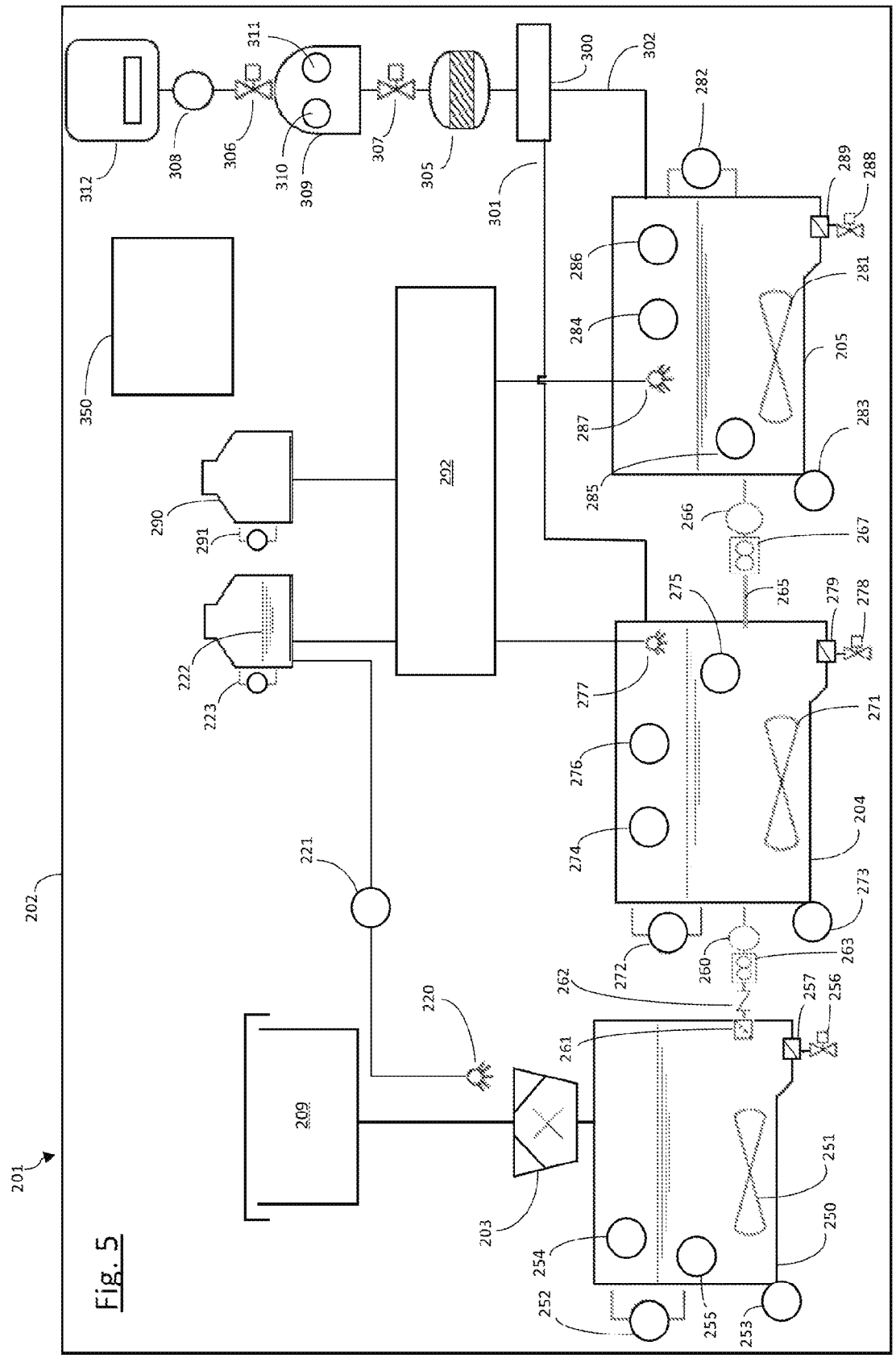
FIG. 5 is a schematic plan of a second example of an anaerobic digestion apparatus.

A second example of anaerobic digestion apparatus 201 is now described with reference to FIG. 5. The structure and function of the second example is generally the same as the first example but with the difference that instead of refrigerating the first digestion chamber, the first digestion chamber is instead heated in use to a temperature of 60-70° C. This again has the effect of suppressing methanogenic microorganisms in the first digestion chamber, as such organisms have a limited optimum range temperature range (for example, *Methanosaeta concilii* has a narrow optimum temperature range, around 35° C.). The higher temperature range has the advantage of pasteurising the food matter slurry, which can be important to meet environmental standards for the reuse of food and/or animal waste and/or to avoid competition between the acidogenic bacteria and the methanogenic archae in the second chamber, during methanogenesis. A storage tank holds macerated waste before it is introduced into the first digestion chamber, and that storage tank is refrigerated, e.g. to around or below 4° C. to reduce odour emission from food waste prior to digestion.

In more detail, the apparatus comprises an external housing 202 containing a macerator 203, a storage chamber 250, a first digestion chamber 204, and a second digestion chamber 205. A sealable inlet 209 for receiving waster food matter extends through the housing 202 to the macerator. A high pressure spray 220, powered by a water pump 221, directs water from a water tank 222, having a level meter 223, into the macerator during maceration.

Macerated food waste is held prior to digestion in the storage chamber 250, where it is refrigerated to equal to or below 4° C. using a refrigerator (not shown). The storage chamber has a mixer 251, level sensor 252, heat exchanger 253, pressure sensor 254, and liquid sensor array 255. A controllable valve 256 extends to a drain through a strainer 257. A controllable one-way pump 260 is provided to controllably move macerated waste from the storage chamber to the first digestion chamber, via a large particle filter 261, check valve 262 and flowmeter 263.

The first digestion chamber 204 has a mixer 271, level gauge 272, heat exchanger 273, pressure sensor 274, liquid sensor array 275, gas sensor array 276, a spray head 277, and a drain with controllable valve 278 and strainer 279. A gas conduit 301 extends from the first digestion chamber to the gas flow control system which is described further below. The first digestion chamber has a heater (not shown).

The first digestion chamber 204 is connected to the second digestion chamber 205 through a conduit 265 having a controllable bidirectional pump 266 and a flowmeter 267.

The second digestion chamber 205 has a mixer 281 level gauge 282, heat exchanger 283, pressure sensor 284, liquid sensor array 285, gas sensor array 286, a spray head 287, and a drain with controllable valve 288 and strainer 289. A gas conduit 301 extends from the first digestion chamber to the gas flow control system which is described further below. The second digestion chamber has a heater (not shown).

The apparatus includes a container 290 for hydrolytic enzymes (in solid or liquid form) and a level sensor 291 (where the enzymes are in liquid form). A liquid control system 292 regulates the supply of water and hydrolytic enzymes to the tanks (water is supplied to the spray 220 and thereby the storage tank, hydrolytic enzymes are supplied to the first digestion tank and water may be supplied to the first or second digestion tanks as appropriate to maintain a desired concentration of solid matter, furthermore evaporated water may be received and recycled for use in dispensing enzymes and/or fed back to the macerator).

A gas flow control system 300 controls the receipt of gas (predominantly steam) from the first digestion chamber through conduit 301 and gas (predominantly biogas) from the second digestion chamber through conduit 302. A filter 305 is provided to filter undesirable species from the gas, e.g. CO, $H_2S$ and/or $NH_3$ filters may be present. Controllable valves 306, 307 and a gas pump 308 regulate the flow of gas into a storage tank 309 which has a pressure sensor 310 and a gas sensor array 311, and from the storage tank to a MicroCHP cogenerator 312.

A controller 350 controls the various sensors and actuators including the liquid flow control system, refrigeration and heating, and the gas flow control system.

The liquid sensor arrays 255, 275, 285 include temperature sensors to enable the accurate control of the temperature of matter within each tank, as well as pH sensors and one or more of carbohydrate, lipid and protein concentration sensors. The gas sensor arrays typically monitor at least $CO_2$, $CH_4$ and VFAs as well as gas temperature.

During operation, the apparatus of the second embodiment is controlled generally as per the first embodiment, with the difference that the temperature of the first digestion chamber is controlled to a (variable) setpoint in the range 60-70° C. The storage tank 250 is refrigerated to around 4° C. and macerated matter is periodically moved to the first digestion chamber 204 by pump 260 where it is mixed with the anaerobic digestion microorganisms, where hydrolytic enzymes are added and where the steps of hydrolysis, acidogenesis and acidogenesis are predominantly carried out. Methanogensis is suppressed (indeed the methanogenic organisms are typically killed by the high temperature in the first digestion chamber). Material is periodically moved from the first chamber to the second chamber and, taking into account measurements of acetic acid in the first chamber and, where required in the other direction. The second digestion chamber is as before controlled to a temperature around the optimum temperature for the methanogenic organisms. As with the first example, an inoculum of *A. woodii*; and *M. concilii* is suitable, in which case the temperature of the second chamber is controlled to around 35° C. Hydrolytic enzymes are dispensed in the first digestion chamber, water is dispensed and matter is moved between the first and second digestion chambers are described above.

Figure 6:
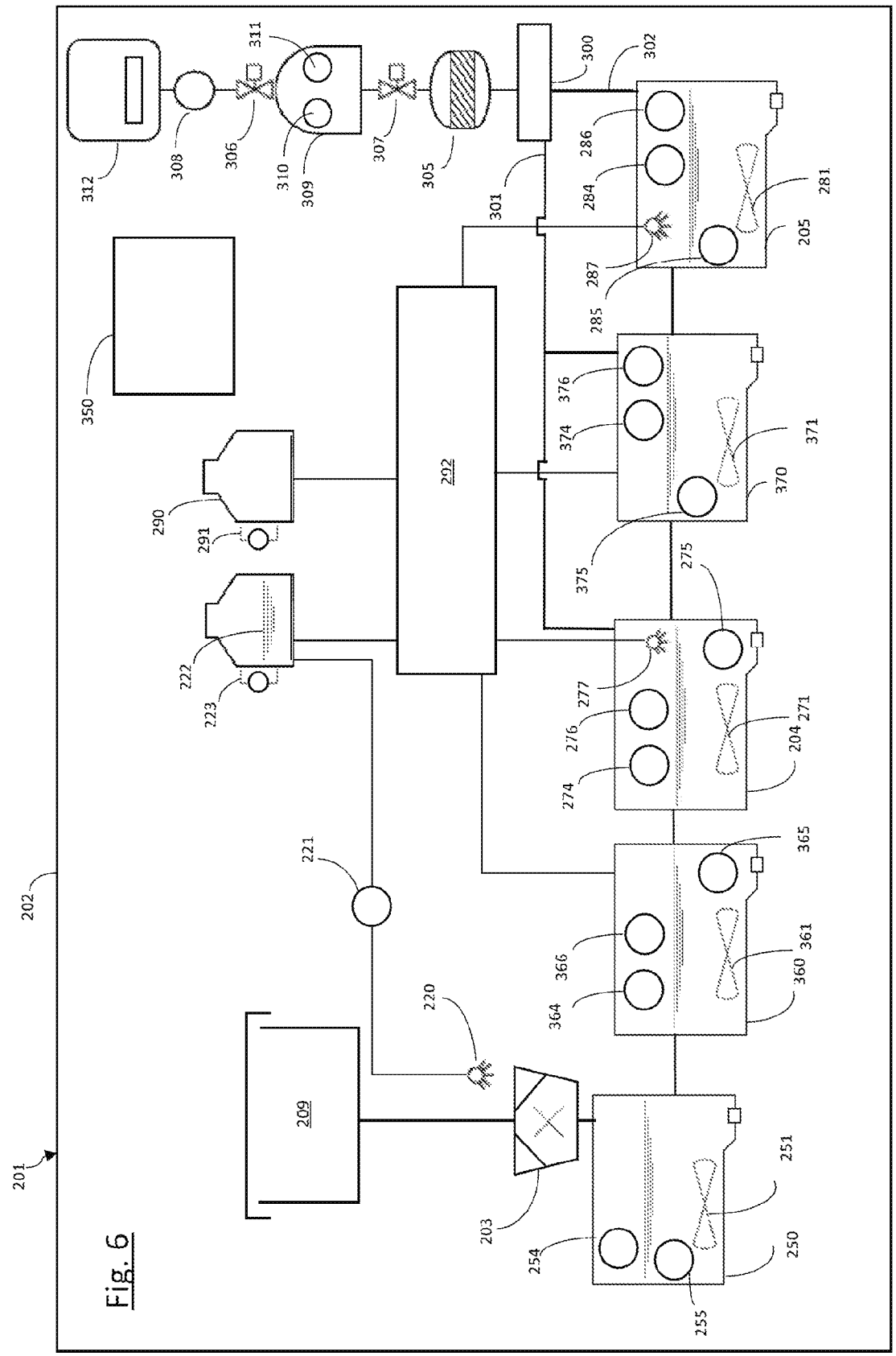
FIG. 6 is a schematic plan of a third example of an anaerobic digestion apparatus.

A third example embodiment is illustrated in FIG. 6. The third example corresponds to the second example except where described and corresponding features are numbered consistently. In FIG. 6, level sensors, heat exchangers and flow control components are omitted for clarity. Again, a controller 350 monitors sensor data and controls the overall procedure.

In the third example embodiment, there are five tanks through which organic matter is moved in a controlled fashion. The first is a storage tank 250 where received macerated waste is refrigerated, to avoid decomposition and the generation of bad smells, and stored until it is further processed. The second tank 360 is a preliminary pasteurisation tank. The third tank 204 is the first digestion chamber, where enzymatic hydrolysis and acidogenesis takes place (and where methanogenesis is suppressed) in use. The fourth tank 370 is a pasteurisation tank. The fifth tank 205 is the second digestion chamber, where methanogenesis takes place in use. Mixers, pressure sensors, liquid sensor arrays and gas sensor arrays in the second tank are labelled 361, 365, 364, 366 respectively and in the fourth tank 371, 375, 374, 376 respectively. As with the other sensors and actuators, including pumps, heaters and coolers, these sensors are connected to the controller 350.

In operation, stored refrigerated waste is controllably moved by a one way pump to the preliminary pasteurisation tank where it is pasteurised, for example at a temperature of 60° C.-70° C. for at least an hour, using a heater (not shown). Water which is evaporated is retained and recycled for use with the macerator (hence the connection shown to the liquid controller from the second tank). In some embodiments, the pressure in the preliminary pasteurisation tank is reduced by a vacuum pump (e.g. such that the boiling point of water is reduced to around 70° C.) to facilitate energy efficient evaporation of water.

After pasteurisation, organic matter is transferred from the preliminary pasteurisation tank to the first digestion chamber 204. Here, the composition of (particularly the nitrogen levels in) the received waste are measured and the controller determines an amount of hydrolytic enzymes to add, and then controls the dispensing of the hydrolytic enzymes. Micro-organisms described before (e.g. *A. woodii* and *M. concilii*) are introduced if not already present and anaerobic digestion begins. (*M. concilii* may be omitted in this tank as methanogenesis is to be avoided, although it may be present either as part of a single inoculum or due to the two-way movement of matter between first and second chambers).

The temperature of this first digestion chamber 204 is regulated as appropriate. In some examples, it may for example be controlled into a range of 50-55° C., for example. This enables efficient acidogenesis and the hydrolytic enzymes can be selected to have a suitable activity at this temperature, however methanogenesis is suppressed. Methanogens such as *M. concilii* are killed at this temperature. In some alternative examples, the first digestion chamber could be heated to a higher temperature (e.g. 60-70° C.) as per the second example, or refrigerated as per the first example below (e.g. to 10° C. or less). In any case, the temperature is selected to minimise methanogenesis.

Material which has been hydrolysis and subject to acidogenesis in the first digestion chamber 204 is than transferred to the further pasterurisation tank 370, where is heated to pasteurise the contents, for example at a temperature of 60-70° C. for at least an hour. Again, water vapour may be collected and the air pressure may be reduced with a vacuum pump. The concentration of VFAs (e.g. at least the concentration of acetic acid) is then measured and used to determine an amount of (or rate of) material to transfer to the fifth tank, the second digestion chamber 205, where methanogenesis is carried out, for example at a temperature of around 35° C.

Material can be occasionally be transferred back from the second digestion chamber to the first digestion chamber, optionally through the further pasteurisation tank, occasionally. This can be useful for example to keep a digester functioning while the controller activates an emergency action, for example one in which it reduces the temperature in the system to below 4° C.

In this example, the fourth tank, the pasteurisation tank 370, functions not only to carry out pasteurisation but also as a buffer tank, which enables material which has been subject to hydrolysis and acidogenesis to be stored so that it can be fed to the second digestion chamber, where methanogenesis is carried out at a controlled rate. VFAs (e.g. at least the concentration of acetic acid) may be measured in the first digestion chamber 204 and used to control the rate of transfer of material from the first digestion chamber 204 to the buffer tank 370. VFAs (e.g. at least the concentration of acetic acid) may be measured in both the first digestion chamber and the buffer tank and used to control the rate of transfer of material from the first digestion chamber to the buffer tank and from the buffer tank to the second digestion chamber.

In a fourth example, however, the first digestion chamber 204 is used to carry out hydrolysis and acidogenesis (at raised or lowered temperature e.g. at 50-55° C., or at 10° C. or below) and then the temperature in the first digestion chamber is raised (e.g. to 60-70° C.) to carry out a pasteurisation step, whereupon VFAs (or at least the concentration of acetic acid) are measured in the resulting material and a controlled amount is transferred to the second digestion chamber 205. In this case, the fourth tank/buffer tank is not required.

Further variations and modifications may be made within the scope of the invention herein disclosed.

The invention claimed is:

1. Anaerobic digestion apparatus comprising a first chamber for retaining organic matter before and/or during anaerobic digestion and a second chamber for retaining organic matter during anaerobic digestion, the anaerobic digestion apparatus being configured to refrigerate the first chamber to thereby suppress methanogenesis in the first chamber, wherein the apparatus is configured to refrigerate the first chamber to a temperature equal to or below 10° C. and to heat the second chamber to a temperature greater than 10° C.

2. The anaerobic digestion apparatus according to claim 1, further comprising one or more sensors configured to measure one or more parameters indicative of volume, mass, composition, protein concentration, concentration of nitrogen-containing species, nitrogen concentration, carbohydrate concentration, lipid concentration, fatty acid concentration, and/or pH of material retained within the first and/or second chambers.

3. The anaerobic digestion apparatus according to claim 2, further comprising a buffer chamber connected to the first and second chambers, through which organic matter is moved from the first to the second chamber, wherein the apparatus is configured to pasteurise organic matter in the buffer chamber.

4. The anaerobic digestion apparatus according to claim 2, further comprising a conduit extending between the first and second chambers, whether directly or through a said buffer chamber, thereby permitting movement of organic matter between the said first and second chambers through the said conduit, flow regulation means for regulating the movement of organic matter between the first and second chambers through the said conduit, and a controller configured to receive measurements of the one or more parameters from the one or more sensors and to regulate the flow of organic matter between the first and second chambers by operating the flow regulation means responsive to the received measurements.

5. The anaerobic digestion apparatus according to claim 2, further comprising a controller configured to receive measurements of the one or more parameters indicative of the protein concentration, the concentration of nitrogen-containing species and/or the nitrogen concentration in the first chamber and to introduce one or more hydrolytic enzymes into the first chamber, wherein the quantity of hydrolytic enzymes introduced into the first chamber is dependent on the value of the one or more parameters.

6. The anaerobic digestion apparatus according claim 1, wherein the apparatus is configured to move organic matter from the first chamber to the second chamber and from the second chamber to the first chamber and therefore to move methanogenic microorganisms from the second chamber to the first chamber.

7. The anaerobic digestion apparatus according to claim 1, further comprising a gas purifier comprising one or more filters configured to remove one or more of the following from gases produced during anaerobic digestion of organic matter in the first and/or second chambers: carbon dioxide, hydrogen sulphide, ammonia.

8. The anaerobic digestion apparatus according to claim 7, further comprising a generator configured to receive a flow of gas from the gas purifier and to output electricity and/or heat generated by combustion of said gas.

9. The anaerobic digestion apparatus according to claim 8, wherein the generator is a micro combined heat and power generator.

10. A method of using the anaerobic digestion apparatus according to claim 1 in the anaerobic digestion of organic matter, the method comprising the steps of: exposing the organic matter to acetogenic microorganisms in the first chamber; transferring at least a portion of the organic matter from the first chamber into the second chamber; and exposing the said at least a portion of the organic matter to methanogenic microorganisms in the second chamber; the method further comprising the steps of refrigerating the first chamber to a temperature equal to or below 10° C. and heating the second chamber to a temperature greater than 10° C.

11. The method according to claim 10, further comprising transferring at least a portion of the organic matter from the second chamber into the first chamber, such that methanogenic microorganisms are transferred into the first chamber from the second chamber, but wherein due to the refrigeration of the first chamber, methanogenesis takes place predominantly in the second chamber.

12. The method according to claim 10, further comprising exposing the organic matter to one or more hydrolytic enzymes in the first chamber.

13. The method according to claim 10, further comprising one or more sensors measuring one or more parameters indicative of volume, mass, composition, protein concentration, concentration of nitrogen-containing species, nitrogen concentration, carbohydrate concentration, lipid concentration, fatty acid concentration, and/or pH of material retained within the first and/or second chambers and/or a buffer chamber, a controller receiving the measurements of the said one or more parameters, and the controller transferring a portion of the organic matter from the first chamber or the buffer chamber to the second chamber responsive to the received measurements.

14. The method according to claim 10, further comprising a gas purifier filtering one or more gases produced during anaerobic digestion of organic matter in the first and/or second chambers to remove one or more of the following from the said gases: carbon dioxide, hydrogen sulphide, ammonia.

15. The method according to claim 10, wherein the acetogenic microorganisms comprise acetogenic bacteria belonging to the genus *Acetobacterium* and the methanogenic microorganisms comprise methanogenic archaea belonging to the genus *Methanosaeta* and/or wherein the acetogenic microorganisms are non-pathogenic and/or the methanogenic microorganisms are non-pathogenic.

16. The method according to claim 10, wherein the method further comprises using digestate as a fertiliser or source of chemical products.

17. The method according to claim 10, further comprising: exposing the organic matter to acetogenic microorganisms at a temperature equal to or below 10° C.; and subsequently exposing at least a portion of the organic matter to methanogenic microorganisms at a temperature greater than 10° C.

18. The method according to claim 17, further comprising exposing the organic matter to one or more hydrolytic enzymes before and/or during the step of exposing the organic matter to acetogenic microorganisms at a temperature equal to or below 10° C.

19. The method according to claim 17, further comprising: exposing the organic matter to both acetogenic microorganisms and methanogenic microorganisms at a temperature equal to or below 10° C.; and subsequently exposing at least a portion of the organic matter to both the acetogenic microorganisms and the methanogenic microorganisms at a temperature greater than 10° C.

\* \* \* \* \*